United States Patent [19]
Edwards et al.

[11] Patent Number: 6,090,931
[45] Date of Patent: Jul. 18, 2000

[54] **PROCESS FOR ALTERING THE HOST RANGE OR INCREASING THE TOXICITY OF *BACILLUS THURINGIENSIS* LEPIDOTERAN TOXINS, AND RECOMBINANT DNA SEQUENCES THEREFOR**

[75] Inventors: David L. Edwards, Del Mar; Corinna Herrnstadt, San Diego; Edward R. Wilcox, Escondido; Siu-Yin Wong, San Diego, all of Calif.

[73] Assignee: Mycogen Corporation, San Diego, Calif.

[21] Appl. No.: 08/855,160

[22] Filed: May 13, 1997

Related U.S. Application Data

[63] Continuation of application No. 08/580,781, Dec. 29, 1995, abandoned, which is a continuation of application No. 08/420,615, Apr. 10, 1995, abandoned, which is a continuation of application No. 08/097,808, Jul. 27, 1993, abandoned, which is a division of application No. 07/980,128, Nov. 23, 1992, abandoned, which is a continuation of application No. 07/803,920, Dec. 6, 1991, abandoned, which is a continuation of application No. 07/356,599, May 24, 1989, abandoned, which is a continuation of application No. 06/904,572, Sep. 5, 1986, abandoned, which is a continuation-in-part of application No. 06/808,129, Dec. 12, 1985, abandoned.

[51] Int. Cl.$^7$ .......................... C12N 15/32; C12N 15/62; C12N 15/70; C12N 15/82
[52] U.S. Cl. ..................... 536/23.71; 435/69.1; 435/440; 435/468; 435/471
[58] Field of Search ........................ 536/23.71; 530/350; 435/172.3, 320.1, 69.1, 440, 468, 471

[56] References Cited

U.S. PATENT DOCUMENTS

| | | | |
|---|---|---|---|
| 4,448,885 | 5/1984 | Schnepf et al. | 435/172.3 |
| 4,467,036 | 8/1984 | Schnepf et al. | 435/172.3 |

OTHER PUBLICATIONS

Schnepf He, et al. *Bacillus thuringiensis* toxins: regulation, activities and structural diversity. Curr. Opinions Biotech. 6: 305–312, 1995.

Schnepf, H. Ernest and H.R. Whiteley (1981) "Cloning and expression of the *Bacillus thuringiensis* crystal protein gene in *Escherichia coli*", Proc. Natl. Acad. Sci. 78(5):2893–2897.

*Primary Examiner*—Lynette R. F. Smith
*Assistant Examiner*—Amy J. Nelson
*Attorney, Agent, or Firm*—Saliwanchik, Lloyd & Saliwanchik

[57] ABSTRACT

The invention concerns an in vitro process for altering the insect host range (spectrum) or increasing the toxicity of lepidopteran active B.t. crystal protein toxins. The process comprises recombining in vitro the variable region(s) (non-homologous) of two or more genes encoding lepidopteran active B.t. crystal protein toxins. Specifically exemplified is the recombining of the variable regions of two genes obtained from well-known strains of *Bacillus thuringiensis* var. *kurstaki*. The resulting products are chimeric toxins which are shown to have an expanded and/or amplified lepidopteran insect host range as compared to the parent toxins.

7 Claims, 4 Drawing Sheets

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 3537 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

```
ATGGATAACA ATCCGAACAT CAATGAATGC ATTCCTTATA ATTGTTTAAG TAACCCTGAA     60
GTAGAAGTAT TAGGTGGAGA AAGAATAGAA ACTGGTTACA CCCCAATCGA TATTTCCTTG    120
TCGCTAACGC AATTTCTTTT GAGTGAATTT GTTCCCGGTG CTGGATTTGT GTTAGGACTA    180
GTTGATATAA TATGGGGAAT TTTTGGTCCC TCTCAATGGG ACGCATTTCC TGTACAAATT    240
GAACAGTTAA TTAACCAAAG AATAGAAGAA TTCGCTAGGA ACCAAGCCAT TTCTAGATTA    300
GAAGGACTAA GCAATCTTTA TCAAATTTAC GCAGAATCTT TTAGAGAGTG GGAAGCAGAT    360
CCTACTAATC CAGCATTAAG AGAAGAGATG CGTATTCAAT TCAATGACAT GAACAGTGCC    420
CTTACAACCG CTATTCCTCT TTTTGCAGTT CAAAATTATC AAGTTCCTCT TTTATCAGTA    480
TATGTTCAAG CTGCAAATTT ACATTTATCA GTTTTGAGAG ATGTTTCAGT GTTTGGACAA    540
AGGTGGGGAT TTGATGCCGC GACTATCAAT AGTCGTTATA ATGATTTAAC TAGGCTTATT    600
GGCAACTATA CAGATTATGC TGTGCGCTGG TACAATACGG GATTAGAGCG TGTATGGGGA    660
CCGGATTCTA GAGATTGGGT AAGGTATAAT CAATTTAGAA GAGAGCTAAC ACTTACTGTA    720
TTAGATATCG TTGCTCTATT CTCAAATTAT GATAGTCGAA GGTATCCAAT TCGAACAGTT    780
TCCCAATTAA CAAGAGAAAT TTATACGAAC CCAGTATTAG AAAATTTTGA TGGTAGTTTT    840
CGTGGAATGG CTCAGAGAAT AGAACAGAAT ATTAGGCAAC CACATCTTAT GGATATCCTT    900
AATAGTATAA CCATTTATAC TGATGTGCAT AGAGGCTTTA ATTATTGGTC AGGGCATCAA    960
ATAACAGCTT CTCCTGTAGG GTTTTCAGGA CCAGAATTCG CATTCCCTTT ATTTGGGAAT   1020
GCGGGGAATG CAGCTCCACC CGTACTTGTC TCATTAACTG GTTTGGGGAT TTTTAGAACA   1080
TTATCTTCAC CTTTATATAG AAGAATTATA CTTGGTTCAG GCCCAAATAA TCAGGAACTG   1140
TTTGTCCTTG ATGGAACGGA GTTTTCTTTT GCCTCCCTAA CGACCAACTT GCCTTCCACT   1200
ATATATAGAC AAAGGGGTAC AGTCGATTCA CTAGATGTAA TACCGCCACA GGATAATAGT   1260
GTACCACCTC GTGCGGGATT TAGCCATCGA TTGAGTCATG TTACAATGCT GAGCCAAGCA   1320
GCTGGAGCAG TTTACACCTT GAGAGCTCAA CGTCCTATGT TCTCTTGGAT ACATCGTAGT   1380
GCTGAATTTA ATAATATAAT TGCATCGGAT AGTATTACTC AAATCCCTGC AGTGAAGGGA   1440
AACTTTCTTT TTAATGGTTC TGTAATTTCA GGACCAGGAT TTACTGGTGG GGACTTAGTT   1500
AGATTAAATA GTAGTGGAAA TAACATTCAG AATAGAGGGT ATATTGAAGT TCCAATTCAC   1560
TTCCCATCGA CATCTACCAG ATATCGAGTT CGTGTACGGT ATGCTTCTGT AACCCCGATT   1620
CACCTCAACG TTAATTGGGG TAATTCATCC ATTTTTTCCA ATACAGTACC AGCTACAGCT   1680
ACGTCATTAG ATAATCTACA ATCAAGTGAT TTTGGTTATT TTGAAAGTGC CAATGCTTTT   1740
ACATCTTCAT TAGGTAATAT AGTAGGTGTT AGAAATTTTA GTGGGACTGC AGGAGTGATA   1800
```

```
ATAGACAGAT TTGAATTTAT TCCAGTTACT GCAACACTCG AGGCTGAATA TAATCTGGAA    1860

AGAGCGCAGA AGGCGGTGAA TGCGCTGTTT ACGTCTACAA ACCAACTAGG GCTAAAAACA    1920

AATGTAACGG ATTATCATAT TGATCAAGTG TCCAATTTAG TTACGTATTT ATCGGATGAA    1980

TTTTGTCTGG ATGAAAAGCG AGAATTGTCC GAGAAAGTCA AACATGCGAA GCGACTCAGT    2040

GATGAACGCA ATTTACTCCA AGATTCAAAT TTCAAAGACA TTAATAGGCA ACCAGAACGT    2100

GGGTGGGGCG GAAGTACAGG GATTACCATC CAAGGAGGGG ATGACGTATT TAAAGAAAAT    2160

TACGTCACAC TATCAGGTAC CTTTGATGAG TGCTATCCAA CATATTTGTA TCAAAAAATC    2220

GATGAATCAA AATTAAAAGC CTTTACCCGT TATCAATTAA GAGGGTATAT CGAAGATAGT    2280

CAAGACTTAG AAATCTATTT AATTCGCTAC AATGCAAAAC ATGAAACAGT AAATGTGCCA    2340

GGTACGGGTT CCTTATGGCC GCTTTCAGCC CAAAGTCCAA TCGGAAAGTG TGGAGAGCCG    2400

AATCGATGCG CGCCACACCT TGAATGGAAT CCTGACTTAG ATTGTTCGTG TAGGGATGGA    2460

GAAAAGTGTG CCCATCATTC GCATCATTTC TCCTTAGACA TTGATGTAGG ATGTACAGAC    2520

TTAAATGAGG ACCTAGGTGT ATGGGTGATC TTTAAGATTA AGACGCAAGA TGGGCACGCA    2580

AGACTAGGGA ATCTAGAGTT TCTCGAAGAG AAACCATTAG TAGGAGAAGC GCTAGCTCGT    2640

GTGAAAAGAG CGGAGAAAAA ATGGAGAGAC AAACGTGAAA AATTGGAATG GAAACAAAT    2700

ATCGTTTATA AAGAGGCAAA AGAATCTGTA GATGCTTTAT TTGTAAACTC TCAATATGAT    2760

CAATTACAAG CGGATACGAA TATTGCCATG ATTCATGCGG CAGATAAACG TGTTCATAGC    2820

ATTCGAGAAG CTTATCTGCC TGAGCTGTCT GTGATTCCGG GTGTCAATGC GGCTATTTTT    2880

GAAGAATTAG AAGGGCGTAT TTTCACTGCA TTCTCCCTAT ATGATGCGAG AAATGTCATT    2940

AAAAATGGTG ATTTTAATAA TGGCTTATCC TGCTGGAACG TGAAAGGGCA TGTAGATGTA    3000

GAAGAACAAA ACAACCAACG TTCGGTCCTT GTTGTTCCGG AATGGGAAGC AGAAGTGTCA    3060

CAAGAAGTTC GTGTCTGTCC GGGTCGTGGC TATATCCTTC GTGTCACAGC GTACAAGGAG    3120

GGATATGGAG AAGGTTGCGT AACCATTCAT GAGATCGAGA ACAATACAGA CGAACTGAAG    3180

TTTAGCAACT GCGTAGAAGA GGAAATCTAT CCAAATAACA CGGTAACGTG TAATGATTAT    3240

ACTGTAAATC AAGAAGAATA CGGAGGTGCG TACACTTCTC GTAATCGAGG ATATAACGAA    3300

GCTCCTTCCG TACCAGCTGA TTATGCGTCA GTCTATGAAG AAAAATCGTA TACAGATGGA    3360

CGAAGAGAGA ATCCTTGTGA ATTTAACAGA GGGTATAGGG ATTACACGCC ACTACCAGTT    3420

GGTTATGTGA CAAAAGAATT AGAATACTTC CCAGAAACCG ATAAGGTATG GATTGAGATT    3480

GGAGAAACGG AAGGAACATT TATCGTGGAC AGCGTGGAAT TACTCCTTAT GGAGGAA      3537
```

(2) INFORMATION FOR SEQ ID NO:2:

(i) SEQUENCE CHARACTERISTICS:
        (A) LENGTH: 1177 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Asp Asn Asn Pro Asn Ile Asn Glu Cys Ile Pro Tyr Asn Cys Leu
1               5                  10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
```

-continued

```
                35                  40                  45
Glu Phe Val Pro Gly Ala Gly Phe Val Leu Gly Leu Val Asp Ile Ile
 50                  55                  60
Trp Gly Ile Phe Gly Pro Ser Gln Trp Asp Ala Phe Leu Val Gln Ile
 65                  70                  75                  80
Glu Gln Leu Ile Asn Gln Arg Ile Glu Glu Phe Ala Arg Asn Gln Ala
                 85                  90                  95
Ile Ser Arg Leu Glu Gly Leu Ser Asn Leu Tyr Gln Ile Tyr Ala Glu
                100                 105                 110
Ser Phe Arg Glu Trp Glu Ala Asp Pro Thr Asn Pro Ala Leu Arg Glu
                115                 120                 125
Glu Met Arg Ile Gln Phe Asn Asp Met Asn Ser Ala Leu Thr Thr Ala
            130                 135                 140
Ile Pro Leu Phe Ala Val Gln Asn Tyr Gln Val Pro Leu Leu Ser Val
145                 150                 155                 160
Tyr Val Gln Ala Ala Asn Leu His Leu Ser Val Leu Arg Asp Val Ser
                    165                 170                 175
Val Phe Gly Gln Arg Trp Gly Phe Asp Ala Ala Thr Ile Asn Ser Arg
                180                 185                 190
Tyr Asn Asp Leu Thr Arg Leu Ile Gly Asn Tyr Thr Asp Tyr Ala Val
                195                 200                 205
Arg Trp Tyr Asn Thr Gly Leu Glu Arg Val Trp Gly Pro Asp Ser Arg
210                 215                 220
Asp Trp Val Arg Tyr Asn Gln Phe Arg Arg Glu Leu Thr Leu Thr Val
225                 230                 235                 240
Leu Asp Ile Val Ala Leu Phe Pro Asn Tyr Asp Ser Arg Arg Tyr Pro
                    245                 250                 255
Ile Arg Thr Val Ser Gln Leu Thr Arg Glu Ile Tyr Thr Asn Pro Val
                260                 265                 270
Leu Glu Asn Phe Asp Gly Ser Phe Arg Gly Ser Ala Gln Gly Ile Glu
                275                 280                 285
Arg Ser Ile Arg Ser Pro His Leu Met Asp Ile Leu Asn Ser Ile Thr
290                 295                 300
Ile Tyr Thr Asp Ala His Arg Gly Tyr Tyr Tyr Trp Ser Gly His Gln
305                 310                 315                 320
Ile Met Ala Ser Pro Val Gly Phe Ser Gly Pro Glu Phe Thr Phe Pro
                325                 330                 335
Leu Tyr Gly Thr Met Gly Asn Ala Ala Pro Gln Gln Arg Ile Val Ala
                340                 345                 350
Gln Leu Gly Gln Gly Val Tyr Arg Thr Leu Ser Ser Thr Leu Tyr Arg
                355                 360                 365
Arg Pro Phe Asn Ile Gly Ile Asn Asn Gln Gln Leu Ser Val Leu Asp
370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
                420                 425                 430
Val Ser Met Phe Arg Ser Gly Phe Ser Asn Ser Ser Val Ser Ile Ile
                435                 440                 445
Arg Ala Pro Thr Phe Ser Trp Gln His Arg Ser Ala Glu Phe Asn Asn
450                 455                 460
```

```
Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
            485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
            565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
            595                 600                 605

Val Thr Phe Glu Ala Glu Tyr Asp Leu Glu Arg Ala Gln Lys Ala Val
610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
            645                 650                 655

Asp Glu Phe Cys Leu Asp Glu Lys Gln Glu Leu Ser Glu Lys Val Lys
            660                 665                 670

His Ala Lys Arg Leu Ser Asp Glu Arg Asn Leu Leu Gln Asp Pro Asn
            675                 680                 685

Phe Arg Gly Ile Asn Arg Gln Leu Asp Arg Gly Trp Arg Gly Ser Thr
690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
            725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
            755                 760                 765

Asn Ala Lys His Glu Thr Val Asn Val Pro Gly Thr Gly Ser Leu Trp
770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
            805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
            835                 840                 845

Phe Lys Ile Lys Thr Gln Asp Gly His Ala Arg Leu Gly Asn Leu Glu
850                 855                 860

Phe Leu Glu Glu Lys Pro Leu Val Gly Glu Ala Leu Ala Arg Val Lys
865                 870                 875                 880
```

```
Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Gln Leu Gln Ala Asp Thr Asn Ile Ala Met
            915                 920                 925

Ile His Ala Ala Asp Lys Arg Val His Ser Ile Arg Glu Ala Tyr Leu
        930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu Gln Asn Asn Gln Arg Ser Val Leu
            995                 1000                1005

Val Leu Pro Glu Trp Glu Ala Glu Val Ser Gln Glu Val Arg Val Cys
    1010                1015                1020

Pro Gly Arg Gly Tyr Ile Leu Arg Val Thr Ala Tyr Lys Glu Gly Tyr
1025                1030                1035                1040

Gly Glu Gly Cys Val Thr Ile His Glu Ile Glu Asn Asn Thr Asp Glu
                1045                1050                1055

Leu Lys Phe Ser Asn Cys Val Glu Glu Glu Ile Tyr Pro Asn Asn Thr
            1060                1065                1070

Val Thr Cys Asn Asp Tyr Thr Val Asn Gln Glu Glu Tyr Gly Gly Ala
            1075                1080                1085

Tyr Thr Ser Arg Asn Arg Gly Tyr Asn Glu Ala Pro Ser Val Pro Ala
    1090                1095                1100

Asp Tyr Ala Ser Val Tyr Glu Glu Lys Ser Tyr Thr Asp Gly Arg Arg
1105                1110                1115                1120

Glu Asn Pro Cys Glu Phe Asn Arg Gly Tyr Arg Asp Tyr Thr Pro Leu
                1125                1130                1135

Pro Val Gly Tyr Val Thr Lys Glu Leu Glu Tyr Phe Pro Glu Thr Asp
            1140                1145                1150

Lys Val Trp Ile Glu Ile Gly Glu Thr Glu Gly Thr Phe Ile Val Asp
            1155                1160                1165

Ser Val Glu Leu Leu Leu Met Glu Glu
    1170                1175

(2) INFORMATION FOR SEQ ID NO:3:

(i) SEQUENCE CHARACTERISTICS:
        (A) LENGTH: 3531 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

ATGGATAACA ATCCGAACAT CAATGAATGC ATTCCTTATA ATTGTTTAAG TAACCCTGAA      60

GTAGAAGTAT TAGGTGGAGA AAGAATAGAA ACTGGTTACA CCCCAATCGA TATTTCCTTG     120

TCGCTAACGC AATTTCTTTT GAGTGAATTT GTTCCCGGTG CTGGATTTGT GTTAGGACTA     180

GTTGATATAA TATGGGGAAT TTTTGGTCCC TCTCAATGGG ACGCATTTCT TGTACAAATT     240

GAACAGTTAA TTAACCAAAG AATAGAAGAA TTCGCTAGGA ACCAAGCCAT TTCTAGATTA     300
```

```
GAAGGACTAA GCAATCTTTA TCAAATTTAC GCAGAATCTT TTAGAGAGTG GGAAGCAGAT      360

CCTACTAATC CAGCATTAAG AGAAGAGATG CGTATTCAAT TCAATGACAT GAACAGTGCC      420

CTTACAACCG CTATTCCTCT TTTTGCAGTT CAAAATTATC AAGTTCCTCT TTTATCAGTA      480

TATGTTCAAG CTGCAAATTT ACATTTATCA GTTTTGAGAG ATGTTTCAGT GTTTGGACAA      540

AGGTGGGGAT TTGATGCCGC GACTATCAAT AGTCGTTATA ATGATTTAAC TAGGCTTATT      600

GGCAACTATA CAGATTATGC TGTACGCTGG TACAATACGG GATTAGAACG TGTATGGGGA      660

CCGGATTCTA GAGATTGGGT AAGGTATAAT CAATTTAGAA GAGAATTAAC ACTAACTGTA      720

TTAGATATCG TTGCTCTGTT CCCGAATTAT GATAGTAGAA GATATCCAAT TCGAACAGTT      780

TCCCAATTAA CAAGAGAAAT TTATACAAAC CCAGTATTAG AAAATTTTGA TGGTAGTTTT      840

CGAGGCTCGG CTCAGGGCAT AGAAAGAAGT ATTAGGAGTC ACATTTGAT GGATATACTT       900

AACAGTATAA CCATCTATAC GGATGCTCAT AGGGGTTATT ATTATTGGTC AGGGCATCAA      960

ATAATGGCTT CTCCTGTAGG GTTTTCGGGG CCAGAATTCA CTTTTCCGCT ATATGGAACT     1020

ATGGGAAATG CAGCTCCACA ACAACGTATT GTTGCTCAAC TAGGTCAGGG CGTGTATAGA     1080

ACATTATCGT CCACTTTATA TAGAAGACCT TTTAATATAG GGATAAATAA TCAACAACTA     1140

TCTGTTCTTG ACGGGACAGA ATTTGCTTAT GGAACCTCCT CAAATTTGCC ATCCGCTGTA     1200

TACAGAAAAA GCGGAACGGT AGATTCGCTG GATGAAATAC CGCCACAGAA TAACAACGTG     1260

CCACCTAGGC AAGGATTTAG TCATCGATTA AGCCATGTTT CAATGTTTCG TTCAGGCTTT     1320

AGTAATAGTA GTGTAAGTAT AATAAGAGCT CCAACGTTTT CTTGGCAGCA TCGCAGTGCT     1380

GAATTTAATA ATATAATTCC TTCATCACAA ATTACACAAA TACCTTTAAC AAAATCTACT     1440

AATCTTGGCT CTGGAACTTC TGTCGTTAAA GGACCAGGAT TTACAGGAGG AGATATTCTT     1500

CGAAGAACTT CACCTGGCCA GATTTCAACC TTAAGAGTAA ATATTACTGC ACCATTATCA     1560

CAAAGATATC GGGTAAGAAT TCGCTACGCT TCTACTACAA ATTTACAATT CCATACATCA     1620

ATTGACGGAA GACCTATTAA TCAGGGTAAT TTTTCAGCAA CTATGAGTAG TGGGAGTAAT     1680

TTACAGTCCG GAAGCTTTAG GACTGTAGGT TTTACTACTC CGTTTAACTT TTCAAATGGA     1740

TCAAGTGTAT TTACGTTAAG TGCTCATGTC TTCAATTCAG GCAATGAAGT TTATATAGAT     1800

CGAATTGAAT TTGTTCCGGC AGAAGTAACC TTTGAGGCAG AATATGATTT AGAAAGAGCA     1860

CAAAAGGCGG TGAATGAGCT GTTTACTTCT TCCAATCAAA TCGGGTTAAA AACAGATGTG     1920

ACGGATTATC ATATTGATCA AGTATCCAAT TTAGTTGAGT GTTTATCAGA TGAATTTTGT     1980

CTGGATGAAA AACAAGAATT GTCCGAGAAA GTCAAACATG CGAAGCGACT TAGTGATGAG     2040

CGGAATTTAC TTCAAGATCC AAACTTCAGA GGGATCAATA GACAACTAGA CCGTGGCTGG     2100

AGAGGAAGTA CGGATATTAC CATCCAAGGA GGCGATGACG TATTCAAAGA GAATTACGTT     2160

ACGCTATTGG GTACCTTTGA TGAGTGCTAT CCAACGTATT TATATCAAAA AATAGATGAG     2220

TCGAAATTAA AAGCCTATAC CCGTTATCAA TTAAGAGGGT ATATCGAAGA TAGTCAAGAC     2280

TTAGAAATCT ATTTAATTCG CTACAATGCA AAACATGAAA CAGTAAATGT GCCAGGTACG     2340

GGTTCCTTAT GGCCGCTTTC AGCCCAAAGT CCAATCGGAA AGTGTGGAGA GCCGAATCGA     2400

TGCGCGCCAC ACCTTGAATG GAATCCTGAC TTAGATTGTT CGTGTAGGGA TGGAGAAAAG     2460

TGTGCCCATC ATTCGCATCA TTTCTCCTTA GACATTGATG TAGGATGTAC AGACTTAAAT     2520

GAGGACCTAG GTGTATGGGT GATCTTTAAG ATTAAGACGC AAGATGGGCA CGCAAGACTA     2580

GGGAATCTAG AGTTTCTCGA AGAGAAACCA TTAGTAGGAG AAGCGCTAGC TCGTGTGAAA     2640
```

-continued

```
AGAGCGGAGA AAAAATGGAG AGACAAACGT GAAAAATTGG AATGGGAAAC AAATATCGTT    2700

TATAAAGAGG CAAAAGAATC TGTAGATGCT TTATTTGTAA ACTCTCAATA TGATCAATTA    2760

CAAGCGGATA CGAATATTGC CATGATTCAT GCGGCAGATA AACGTGTTCA TAGCATTCGA    2820

GAAGCTTATC TGCCTGAGCT GTCTGTGATT CCGGGTGTCA ATGCGGCTAT TTTTGAAGAA    2880

TTAGAAGGGC GTATTTTCAC TGCATTCTCC CTATATGATG CGAGAAATGT CATTAAAAAT    2940

GGTGATTTTA ATAATGGCTT ATCCTGCTGG AACGTGAAAG GGCATGTAGA TGTAGAAGAA    3000

CAAAACAACC AACGTTCGGT CCTTGTTCTT CCGGAATGGG AAGCAGAAGT GTCACAAGAA    3060

GTTCGTGTCT GTCCGGGTCG TGGCTATATC CTTCGTGTCA CAGCGTACAA GGAGGGATAT    3120

GGAGAAGGTT GCGTAACCAT TCATGAGATC GAGAACAATA CAGACGAACT GAAGTTTAGC    3180

AACTGCGTAG AAGAGGAAAT CTATCCAAAT AACACGGTAA CGTGTAATGA TTATACTGTA    3240

AATCAAGAAG AATACGGAGG TGCGTACACT TCTCGTAATC GAGGATATAA CGAAGCTCCT    3300

TCCGTACCAG CTGATTATGC GTCAGTCTAT GAAGAAAAAT CGTATACAGA TGGACGAAGA    3360

GAGAATCCTT GTGAATTTAA CAGAGGGTAT AGGGATTACA CGCCACTACC AGTTGGTTAT    3420

GTGACAAAAG AATTAGAATA CTTCCCAGAA ACCGATAAGG TATGGATTGA GATTGGAGAA    3480

ACGGAAGGAA CATTTATCGT GGACAGCGTG GAATTACTCC TTATGGAGGA A             3531
```

(2) INFORMATION FOR SEQ ID NO:4:

(i) SEQUENCE CHARACTERISTICS:
        (A) LENGTH: 1179 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Asp Asn Asn Pro Asn Ile Asn Glu Cys Ile Pro Tyr Asn Cys Leu
1               5                  10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Pro Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190
```

-continued

```
Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Met Ala Gln Arg Ile Glu
            275                 280                 285

Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
            355                 360                 365

Ile Ile Leu Gly Ser Gly Pro Asn Asn Gln Glu Leu Phe Val Leu Asp
370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
            435                 440                 445

Ala Gln Arg Pro Met Phe Ser Trp Ile His Arg Ser Ala Glu Phe Asn
    450                 455                 460

Asn Ile Ile Ala Ser Asp Ser Ile Thr Gln Ile Pro Ala Val Lys Gly
465                 470                 475                 480

Asn Phe Leu Phe Asn Gly Ser Val Ile Ser Gly Pro Gly Phe Thr Gly
                485                 490                 495

Gly Asp Leu Val Arg Leu Asn Ser Ser Gly Asn Asn Ile Gln Asn Arg
            500                 505                 510

Gly Tyr Ile Glu Val Pro Ile His Phe Pro Ser Thr Ser Thr Arg Tyr
        515                 520                 525

Arg Val Arg Val Arg Tyr Ala Ser Val Thr Pro Ile His Leu Asn Val
530                 535                 540

Asn Trp Gly Asn Ser Ser Ile Phe Ser Asn Thr Val Pro Ala Thr Ala
545                 550                 555                 560

Thr Ser Leu Asp Asn Leu Gln Ser Ser Asp Phe Gly Tyr Phe Glu Ser
                565                 570                 575

Ala Asn Ala Phe Thr Ser Ser Leu Gly Asn Ile Val Gly Val Arg Asn
            580                 585                 590

Phe Ser Gly Thr Ala Gly Val Ile Ile Asp Arg Phe Glu Phe Ile Pro
            595                 600                 605

Val Thr Ala Thr Leu Glu Ala Glu Tyr Asn Leu Glu Arg Ala Gln Lys
```

-continued

```
            610                 615                 620
Ala Val Asn Ala Leu Phe Thr Ser Thr Asn Gln Leu Gly Leu Lys Thr
625                 630                 635                 640
Asn Val Thr Asp Tyr His Ile Asp Gln Val Ser Asn Leu Val Thr Tyr
                    645                 650                 655
Leu Ser Asp Glu Phe Cys Leu Asp Glu Lys Arg Glu Leu Ser Glu Lys
                660                 665                 670
Val Lys His Ala Lys Arg Leu Ser Asp Glu Arg Asn Leu Leu Gln Asp
            675                 680                 685
Ser Asn Phe Lys Asp Ile Asn Arg Gln Pro Glu Arg Gly Trp Gly Gly
690                 695                 700
Ser Thr Gly Ile Thr Ile Gln Gly Gly Asp Asp Val Phe Lys Glu Asn
705                 710                 715                 720
Tyr Val Thr Leu Ser Gly Thr Phe Asp Glu Cys Tyr Pro Thr Tyr Leu
                    725                 730                 735
Tyr Gln Lys Ile Asp Glu Ser Lys Leu Lys Ala Phe Thr Arg Tyr Gln
                740                 745                 750
Leu Arg Gly Tyr Ile Glu Asp Ser Gln Asp Leu Glu Ile Tyr Leu Ile
            755                 760                 765
Arg Tyr Asn Ala Lys His Glu Thr Val Asn Val Pro Gly Thr Gly Ser
770                 775                 780
Leu Trp Pro Leu Ser Ala Gln Ser Pro Ile Gly Lys Cys Gly Glu Pro
785                 790                 795                 800
Asn Arg Cys Ala Pro His Leu Glu Trp Asn Pro Asp Leu Asp Cys Ser
                    805                 810                 815
Cys Arg Asp Gly Glu Lys Cys Ala His His Ser His His Phe Ser Leu
                820                 825                 830
Asp Ile Asp Val Gly Cys Thr Asp Leu Asn Glu Asp Leu Gly Val Trp
            835                 840                 845
Val Ile Phe Lys Ile Lys Thr Gln Asp Gly His Ala Arg Leu Gly Asn
850                 855                 860
Leu Glu Phe Leu Glu Glu Lys Pro Leu Val Gly Glu Ala Leu Ala Arg
865                 870                 875                 880
Val Lys Arg Ala Glu Lys Lys Trp Arg Asp Lys Arg Glu Lys Leu Glu
                885                 890                 895
Trp Glu Thr Asn Ile Val Tyr Lys Glu Ala Lys Glu Ser Val Asp Ala
                900                 905                 910
Leu Phe Val Asn Ser Gln Tyr Asp Gln Leu Gln Ala Asp Thr Asn Ile
            915                 920                 925
Ala Met Ile His Ala Ala Asp Lys Arg Val His Ser Ile Arg Glu Ala
930                 935                 940
Tyr Leu Pro Glu Leu Ser Val Ile Pro Gly Val Asn Ala Ala Ile Phe
945                 950                 955                 960
Glu Glu Leu Glu Gly Arg Ile Phe Thr Ala Phe Ser Leu Tyr Asp Ala
                965                 970                 975
Arg Asn Val Ile Lys Asn Gly Asp Phe Asn Asn Gly Leu Ser Cys Trp
                980                 985                 990
Asn Val Lys Gly His Val Asp Val Glu Glu Gln Asn Asn Gln Arg Ser
            995                 1000                1005
Val Leu Val Val Pro Glu Trp Glu Ala Glu Val Ser Gln Glu Val Arg
    1010                1015                1020
Val Cys Pro Gly Arg Gly Tyr Ile Leu Arg Val Thr Ala Tyr Lys Glu
1025                1030                1035                1040
```

```
Gly Tyr Gly Glu Gly Cys Val Thr Ile His Glu Ile Glu Asn Asn Thr
                1045                1050                1055

Asp Glu Leu Lys Phe Ser Asn Cys Val Glu Glu Glu Ile Tyr Pro Asn
            1060                1065                1070

Asn Thr Val Thr Cys Asn Asp Tyr Thr Val Asn Gln Glu Glu Tyr Gly
        1075                1080                1085

Gly Ala Tyr Thr Ser Arg Asn Arg Gly Tyr Asn Glu Ala Pro Ser Val
    1090                1095                1100

Pro Ala Asp Tyr Ala Ser Val Tyr Glu Glu Lys Ser Tyr Thr Asp Gly
1105                1110                1115                1120

Arg Arg Glu Asn Pro Cys Glu Phe Asn Arg Gly Tyr Arg Asp Tyr Thr
                1125                1130                1135

Pro Leu Pro Val Gly Tyr Val Thr Lys Glu Leu Glu Tyr Phe Pro Glu
            1140                1145                1150

Thr Asp Lys Val Trp Ile Glu Ile Gly Glu Thr Glu Gly Thr Phe Ile
            1155                1160                1165

Val Asp Ser Val Glu Leu Leu Leu Met Glu Glu
        1170                1175

(2) INFORMATION FOR SEQ ID NO:5:

(i) SEQUENCE CHARACTERISTICS:
        (A) LENGTH: 3531 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

ATGGATAACA ATCCGAACAT CAATGAATGC ATTCCTTATA ATTGTTTAAG TAACCCTGAA      60

GTAGAAGTAT TAGGTGGAGA AGAATAGAAA ACTGGTTACA CCCCAATCGA TATTTCCTTG     120

TCGCTAACGC AATTTCTTTT GAGTGAATTT GTTCCCGGTG CTGGATTTGT GTTAGGACTA     180

GTTGATATAA TATGGGGAAT TTTTGGTCCC TCTCAATGGG ACGCATTTCT TGTACAAATT     240

GAACAGTTAA TTAACCAAAG AATAGAAGAA TTCGCTAGGA ACCAAGCCAT TTCTAGATTA     300

GAAGGACTAA GCAATCTTTA TCAAATTTAC GCAGAATCTT TTAGAGAGTG GGAAGCAGAT     360

CCTACTAATC CAGCATTAAG AGAAGAGATG CGTATTCAAT TCAATGACAT GAACAGTGCC     420

CTTACAACCG CTATTCCTCT TTTTGCAGTT CAAAATTATC AAGTTCCTCT TTTATCAGTA     480

TATGTTCAAG CTGCAAATTT ACATTTATCA GTTTTGAGAG ATGTTTCAGT GTTTGGACAA     540

AGGTGGGGAT TGATGCCGC GACTATCAAT AGTCGTTATA ATGATTAAC TAGGCTTATT      600

GGCAACTATA CAGATTATGC TGTACGCTGG TACAATACGG GATTAGAACG TGTATGGGGA     660

CCGGATTCTA GAGATTGGGT AAGGTATAAT CAATTTAGAA GAGAATTAAC ACTAACTGTA     720

TTAGATATCG TTGCTCTGTT CCCGAATTAT GATAGTAGAA GATATCCAAT TCGAACAGTT     780

TCCCAATTAA CAAGAGAAAT TTATACAAAC CCAGTATTAG AAAATTTTGA TGGTAGTTTT     840

CGAGGCTCGG CTCAGGGCAT AGAAAGAAGT ATTAGGAGTC CACATTTGAT GGATATACTT     900

AACAGTATAA CCATCTATAC GGATGCTCAT AGGGGTTATT ATTATTGGTC AGGGCATCAA     960

ATAATGGCTT CTCCTGTAGG GTTTTCGGGG CCAGAATTCA CTTTTCCGCT ATATGGAACT    1020

ATGGGAAATG CAGCTCCACA ACAACGTATT GTTGCTCAAC TAGGTCAGGG CGTGTATAGA    1080

ACATTATCGT CCACTTTATA TAGAAGACCT TTTAATATAG GGATAAATAA TCAACAACTA    1140
```

-continued

```
TCTGTTCTTG ACGGGACAGA ATTTGCTTAT GGAACCTCCT CAAATTTGCC ATCCGCTGTA      1200

TACAGAAAAA GCGGAACGGT AGATTCGCTG AATGAAATAC CGCCACAGAA TAACAACGTG      1260

CCACCTAGGC AAGAATTTAG TCATCGATTA AGCCATGTTT CAATGTTTCG TTCAGGCTTT      1320

AGTAATAGTA GTGTAAGTAT AATAAGAGCT CCAACGTTTT CTTGGCAGCA TCGCAGTGCT      1380

GAATTTAATA ATATAATTCC TTCATCACAA ATTACACAAA TACCTTTAAC AAAATCTACT      1440

AATCTTGGCT CTGGAACTTC TGTCGTTAAA GGACCAGGAT TTACAGGAGG AGATATTCTT      1500

CGAAGAACTT CACCTGGCCA GATTTCAACC TTAAGAGTAA ATATTACTGC ACCATTATCA      1560

CAAAGATATC GGGTAAGAAT TCGCTACGCT TCTACTACAA ATTTACAATT CCATACATCA      1620

ATTGACGGAA GACCTATTAA TCAGGGTAAT TTTTCAGCAA CTATGAGTAG TGGGAGTAAT      1680

TTACAGTCCG GAAGCTTTAG GACTGTAGGT TTTACTACTC CGTTTAACTT TTCAAATGGA      1740

TCAAGTGTAT TTACGTTAAG TGCTCATGTC TTCAATTCAG GCAATGAAGT TTATATAGAT      1800

CGAATTGAAT TTGTTCCGGC AGAAGTAACC TTTGAGGCAG AATATGATTT AGAAAGAGCA      1860

CAAAAGGCGG TGAATGAGCT GTTTACTTCT TCCAATCAAA TCGGGTTAAA AACAGATGTG      1920

ACGGATTATC ATATTGATCA AGTATCCAAT TTAGTTGAGT GTTTATCAGA TGAATTTTGT      1980

CTGGATGAAA AACAAGAATT GTCCGAGAAA GTCAAACATG CGAAGCGACT TAGTGATGAG      2040

CGGAATTTAC TTCAAGATCC AAACTTCAGA GGGATCAATA GACAACTAGA CCGTGGCTGG      2100

AGAGGAAGTA CGGATATTAC CATCCAAGGA GGCGATGACG TATTCAAAGA GAATTACGTT      2160

ACGCTATTGG GTACCTTTGA TGAGTGCTAT CCAACGTATT TATATCAAAA AATAGATGAG      2220

TCGAAATTAA AAGCCTATAC CCGTTATCAA TTAAGAGGGT ATATCGAAGA TAGTCAAGAC      2280

TTAGAAATCT ATTTAATTCG CTACAATGCA AAACATGAAA CAGTAAATGT GCCAGGTACG      2340

GGTTCCTTAT GGCCGCTTTC AGCCCAAAGT CCAATCGGAA AGTGTGGAGA GCCGAATCGA      2400

TGCGCGCCAC ACCTTGAATG GAATCCTGAC TTAGATTGTT CGTGTAGGGA TGGAGAAAAG      2460

TGTGCCCATC ATTCGCATCA TTTCTCCTTA GACATTGATG TAGGATGTAC AGACTTAAAT      2520

GAGGACCTAG GTGTATGGGT GATCTTTAAG ATTAAGACGC AAGATGGGCA CGCAAGACTA      2580

GGGAATCTAG AGTTTCTCGA AGAGAAACCA TTAGTAGGAG AAGCGCTAGC TCGTGTGAAA      2640

AGAGCGGAGA AAAAATGGAG AGACAAACGT GAAAAATTGG AATGGGAAAC AAATATCGTT      2700

TATAAAGAGG CAAAAGAATC TGTAGATGCT TTATTTGTAA ACTCTCAATA TGATCAATTA      2760

CAAGCGGATA CGAATATTGC CATGATTCAT GCGGCAGATA AACGTGTTCA TAGCATTCGA      2820

GAAGCTTATC TGCCTGAGCT GTCTGTGATT CCGGGTGTCA ATGCGGCTAT TTTTGAAGAA      2880

TTAGAAGGGC GTATTTTCAC TGCATTCTCC CTATATGATG CGAGAAATGT CATTAAAAAT      2940

GGTGATTTTA ATAATGGCTT ATCCTGCTGG AACGTGAAAG GGCATGTAGA TGTAGAAGAA      3000

CAAAACAACC AACGTTCGGT CCTTGTTCTT CCGGAATGGG AAGCAGAAGT GTCACAAGAA      3060

GTTCGTGTCT GTCCGGGTCG TGGCTATATC CTTCGTGTCA CAGCGTACAA GGAGGGATAT      3120

GGAGAAGGTT GCGTAACCAT TCATGAGATC GAGAACAATA CAGACGAACT GAAGTTTAGC      3180

AACTGCGTAG AAGAGGAAAT CTATCCAAAT AACACGGTAA CGTGTAATGA TTATACTGTA      3240

AATCAAGAAG AATACGGAGG TGCGTACACT TCTCGTAATC GAGGATATAA CGAAGCTCCT      3300

TCCGTACCAG CTGATTATGC GTCAGTCTAT GAAGAAAAAT CGTATACAGA TGGACGAAGA      3360

GAGAATCCTT GTGAATTTAA CAGAGGGTAT AGGGATTACA CGCCACTACC AGTTGGTTAT      3420

GTGACAAAAG AATTAGAATA CTTCCCAGAA ACCGATAAGG TATGGATTGA GATTGGAGAA      3480

ACGGAAGGAA CATTTATCGT GGACAGCGTG GAATTACTCC TTATGGAGGA A              3531
```

(2) INFORMATION FOR SEQ ID NO:6:

(i) SEQUENCE CHARACTERISTICS:
        (A) LENGTH: 1177 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
                35                  40                  45

Glu Phe Val Pro Gly Ala Gly Phe Val Leu Gly Leu Val Asp Ile Ile
 50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350
```

```
Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
        370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asn Glu Ile Pro Pro Gln
                405                 410                 415

Asn Asn Asn Val Pro Pro Arg Gln Glu Phe Ser His Arg Leu Ser His
                420                 425                 430

Val Ser Met Phe Arg Ser Gly Phe Ser Asn Ser Val Ser Ile Ile
            435                 440                 445

Arg Ala Pro Thr Phe Ser Trp Gln His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
                500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
            530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
            595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Gln Glu Leu Ser Glu Lys Val Lys
            660                 665                 670

His Ala Lys Arg Leu Ser Asp Glu Arg Asn Leu Leu Gln Asp Pro Asn
            675                 680                 685

Phe Arg Gly Ile Asn Arg Gln Leu Asp Arg Gly Trp Arg Gly Ser Thr
    690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
                740                 745                 750

Gly Tyr Ile Glu Asp Ser Gln Asp Leu Glu Ile Tyr Leu Ile Arg Tyr
            755                 760                 765
```

-continued

```
Asn Ala Lys His Glu Thr Val Asn Val Pro Gly Thr Gly Ser Leu Trp
    770                 775                 780
Pro Leu Ser Ala Gln Ser Pro Ile Gly Lys Cys Gly Glu Pro Asn Arg
785                 790                 795                 800
Cys Ala Pro His Leu Glu Trp Asn Pro Asp Leu Asp Cys Ser Cys Arg
                805                 810                 815
Asp Gly Glu Lys Cys Ala His Ser His His Phe Ser Leu Asp Ile
                820                 825                 830
Asp Val Gly Cys Thr Asp Leu Asn Glu Asp Leu Gly Val Trp Val Ile
                835                 840                 845
Phe Lys Ile Lys Thr Gln Asp Gly His Ala Arg Leu Gly Asn Leu Glu
                850                 855                 860
Phe Leu Glu Glu Lys Pro Leu Val Gly Glu Ala Leu Ala Arg Val Lys
865                 870                 875                 880
Arg Ala Glu Lys Lys Trp Arg Asp Lys Arg Glu Lys Leu Glu Trp Glu
                885                 890                 895
Thr Asn Ile Val Tyr Lys Glu Ala Lys Glu Ser Val Asp Ala Leu Phe
                900                 905                 910
Val Asn Ser Gln Tyr Asp Gln Leu Gln Ala Asp Thr Asn Ile Ala Met
                915                 920                 925
Ile His Ala Ala Asp Lys Arg Val His Ser Ile Arg Glu Ala Tyr Leu
                930                 935                 940
Pro Glu Leu Ser Val Ile Pro Gly Val Asn Ala Ala Ile Phe Glu Glu
945                 950                 955                 960
Leu Glu Gly Arg Ile Phe Thr Ala Phe Ser Leu Tyr Asp Ala Arg Asn
                965                 970                 975
Val Ile Lys Asn Gly Asp Phe Asn Asn Gly Leu Ser Cys Trp Asn Val
                980                 985                 990
Lys Gly His Val Asp Val Glu Glu Gln Asn Asn Gln Arg Ser Val Leu
                995                 1000                1005
Val Leu Pro Glu Trp Glu Ala Glu Val Ser Gln Glu Val Arg Val Cys
    1010                1015                1020
Pro Gly Arg Gly Tyr Ile Leu Arg Val Thr Ala Tyr Lys Glu Gly Tyr
1025                1030                1035                1040
Gly Glu Gly Cys Val Thr Ile His Glu Ile Glu Asn Asn Thr Asp Glu
                1045                1050                1055
Leu Lys Phe Ser Asn Cys Val Glu Glu Glu Ile Tyr Pro Asn Asn Thr
                1060                1065                1070
Val Thr Cys Asn Asp Tyr Thr Val Asn Gln Glu Glu Tyr Gly Gly Ala
                1075                1080                1085
Tyr Thr Ser Arg Asn Arg Gly Tyr Asn Glu Ala Pro Ser Val Pro Ala
    1090                1095                1100
Asp Tyr Ala Ser Val Tyr Glu Glu Lys Ser Tyr Thr Asp Gly Arg Arg
1105                1110                1115                1120
Glu Asn Pro Cys Glu Phe Asn Arg Gly Tyr Arg Asp Tyr Thr Pro Leu
                1125                1130                1135
Pro Val Gly Tyr Val Thr Lys Glu Leu Glu Tyr Phe Pro Glu Thr Asp
                1140                1145                1150
Lys Val Trp Ile Glu Ile Gly Glu Thr Glu Gly Thr Phe Ile Val Asp
                1155                1160                1165
Ser Val Glu Leu Leu Leu Met Glu Glu
    1170                1175
```

(2) INFORMATION FOR SEQ ID NO:7:

(i) SEQUENCE CHARACTERISTICS:
        (A) LENGTH: 3531 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
ATGGATAACA ATCCGAACAT CAATGAATGC ATTCCTTATA ATTGTTTAAG TAACCCTGAA      60
GTAGAAGTAT TAGGTGGAGA AAGAATAGAA ACTGGTTACA CCCCAATCGA TATTTCCTTG     120
TCGCTAACGC AATTTCTTTT GAGTGAATTT GTTCCCGGTG CTGGATTTGT GTTAGGACTA     180
GTTGATATAA TATGGGGAAT TTTTGGTCCC TCTCAATGGG ACGCATTTCT TGTACAAATT     240
GAACAGTTAA TTAACCAAAG AATAGAAGAA TTCGCTAGGA ACCAAGCCAT TTCTAGATTA     300
GAAGGACTAA GCAATCTTTA TCAAATTTAC GCAGAATCTT TTAGAGAGTG GGAAGCAGAT     360
CCTACTAATC CAGCATTAAG AGAAGAGATG CGTATTCAAT TCAATGACAT GAACAGTGCC     420
CTTACAACCG CTATTCCTCT TTTTGCAGTT CAAAATTATC AAGTTCCTCT TTTATCAGTA     480
TATGTTCAAG CTGCAAATTT ACATTTATCA GTTTTGAGAG ATGTTTCAGT GTTTGGACAA     540
AGGTGGGGAT TTGATGCCGC GACTATCAAT AGTCGTTATA ATGATTTAAC TAGGCTTATT     600
GGCAACTATA CAGATTATGC TGTACGCTGG TACAATACGG GATTAGAACG TGTATGGGGA     660
CCGGATTCTA GAGATTGGGT AAGGTATAAT CAATTTAGAA GAGAATTAAC ACTAACTGTA     720
TTAGATATCG TTGCTCTGTT CCCGAATTAT GATAGTAGAA GATATCCAAT TCGAACAGTT     780
TCCCAATTAA CAAGAGAAAT TTATACAAAC CCAGTATTAG AAAATTTTGA TGGTAGTTTT     840
CGAGGCTCGG CTCAGGGCAT AGAAGGAAGT ATTAGGAGTC CACATTTGAT GGATATACTT     900
AACAGTATAA CCATCTATAC GGATGCTCAT AAAGGGGAAT ATTATTGGTC AGGGCATCAA     960
ATAATGGCTT CTCCTGTAGG GTTTTCGGGG CCAGAATTCA CTTTTCCGCT ATATGGAACT    1020
ATGGGAAATG CAGCTCCACA ACAACGTATT GTTGCTCAAC TAGGTCAGGG CGTGTATAGA    1080
ACATTATCGT CCACTTTATA TAGAAGACCT TTTAATATAG GGATAAATAA TCAACAACTA    1140
TCTGTTCTTG ACGGGACAGA ATTTGCTTAT GGAACCTCCT CAAATTTGCC ATCCGCTGTA    1200
TACAGAAAAA GCGGAACGGT AGATTCGCTG GATGAAATAC CGCCACAGAA TAACAACGTG    1260
CCACCTAGGC AAGGATTTAG TCATCGATTA AGCCATGTTT CAATGTTTCG TTCAGGCTTT    1320
AGTAATAGTA GTGTAAGTAT AATAAGAGCT CCAACGTTTT CTTGGCAGCA TCGCAGTGCT    1380
GAATTTAATA ATATAATTCC TTCATCACAA ATTACACAAA TACCTTTAAC AAAATCTACT    1440
AATCTTGGCT CTGGAACTTC TGTCGTTAAA GGACCAGGAT TTACAGGAGG AGATATTCTT    1500
CGAAGAACTT CACCTGGCCA GATTTCAACC TTAAGAGTAA ATATTACTGC ACCATTATCA    1560
CAAAGATATC GGGTAAGAAT TCGCTACGCT TCTACTACAA ATTTACAATT CCATACATCA    1620
ATTGACGGAA GACCTATTAA TCAGGGTAAT TTTTCAGCAA CTATGAGTAG TGGGAGTAAT    1680
TTACAGTCCG GAAGCTTTAG GACTGTAGGT TTTACTACTC CGTTTAACTT TCAAATGGA    1740
TCAAGTGTAT TTACGTTAAG TGCTCATGTC TTCAATTCAG GCAATGAAGT TTATATAGAT    1800
CGAATTGAAT TTGTTCCGGC AGAAGTAACC TTTGAGGCAG AATATGATTT AGAAAGAGCA    1860
CAAAAGGCGG TGAATGAGCT GTTTACTTCT TCCAATCAAA TCGGGTTAAA AACAGATGTG    1920
ACGGATTATC ATATTGATCA AGTATCCAAT TTAGTTGAGT GTTTATCAGA TGAATTTTGT    1980
CTGGATGAAA AACAAGAATT GTCCGAGAAA GTCAAACATG CGAAGCGACT TAGTGATGAG    2040
```

-continued

```
CGGAATTTAC TTCAAGATCC AAACTTCAGA GGGATCAATA GACAACTAGA CCGTGGCTGG      2100

AGAGGAAGTA CGGATATTAC CATCCAAGGA GGCGATGACG TATTCAAAGA GAATTACGTT      2160

ACGCTATTGG GTACCTTTGA TGAGTGCTAT CCAACGTATT TATATCAAAA AATAGATGAG      2220

TCGAAATTAA AAGCCTATAC CCGTTATCAA TTAAGAGGGT ATATCGAAGA TAGTCAAGAC      2280

TTAGAAATCT ATTTAATTCG CTACAATGCA AAACATGAAA CAGTAAATGT GCCAGGTACG      2340

GGTTCCTTAT GGCCGCTTTC AGCCCAAAGT CCAATCGGAA AGTGTGGAGA GCCGAATCGA      2400

TGCGCGCCAC ACCTTGAATG GAATCCTGAC TTAGATTGTT CGTGTAGGGA TGGAGAAAAG      2460

TGTGCCCATC ATTCGCATCA TTTCTCCTTA GACATTGATG TAGGATGTAC AGACTTAAAT      2520

GAGGACCTAG GTGTATGGGT GATCTTTAAG ATTAAGACGC AAGATGGGCA CGCAAGACTA      2580

GGGAATCTAG AGTTTCTCGA AGAGAAACCA TTAGTAGGAG AAGCGCTAGC TCGTGTGAAA      2640

AGAGCGGAGA AAAAATGGAG AGACAAACGT GAAAAATTGG AATGGGAAAC AAATATCGTT      2700

TATAAAGAGG CAAAAGAATC TGTAGATGCT TTATTTGTAA ACTCTCAATA TGATCAATTA      2760

CAAGCGGATA CGAATATTGC CATGATTCAT GCGGCAGATA AACGTGTTCA TAGCATTCGA      2820

GAAGCTTATC TGCCTGAGCT GTCTGTGATT CCGGGTGTCA ATGCGGCTAT TTTTGAAGAA      2880

TTAGAAGGGC GTATTTTCAC TGCATTCTCC CTATATGATG CGAGAAATGT CATTAAAAAT      2940

GGTGATTTTA ATAATGGCTT ATCCTGCTGG AACGTGAAAG GGCATGTAGA TGTAGAAGAA      3000

CAAAACAACC AACGTTCGGT CCTTGTTCTT CCGGAATGGG AAGCAGAAGT GTCACAAGAA      3060

GTTCGTGTCT GTCCGGGTCG TGGCTATATC CTTCGTGTCA CAGCGTACAA GGAGGGATAT      3120

GGAGAAGGTT GCGTAACCAT TCATGAGATC GAGAACAATA CAGACGAACT GAAGTTTAGC      3180

AACTGCGTAG AAGAGGAAAT CTATCCAAAT AACACGGTAA CGTGTAATGA TTATACTGTA      3240

AATCAAGAAG AATACGGAGG TGCGTACACT TCTCGTAATC GAGGATATAA CGAAGCTCCT      3300

TCCGTACCAG CTGATTATGC GTCAGTCTAT GAAGAAAAAT CGTATACAGA TGGACGAAGA      3360

GAGAATCCTT GTGAATTTAA CAGAGGGTAT AGGGATTACA CGCCACTACC AGTTGGTTAT      3420

GTGACAAAAG AATTAGAATA CTTCCCAGAA ACCGATAAGG TATGGATTGA GATTGGAGAA      3480

ACGGAAGGAA CATTTATCGT GGACAGCGTG GAATTACTCC TTATGGAGGA A             3531
```

(2) INFORMATION FOR SEQ ID NO:8:

(i) SEQUENCE CHARACTERISTICS:
        (A) LENGTH: 1177 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Met Asp Asn Asn Pro Asn Ile Asn Glu Cys Ile Pro Tyr Asn Cys Leu
1               5                  10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80
```

```
Glu Gln Leu Ile Asn Gln Arg Ile Glu Phe Ala Arg Asn Gln Ala
             85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
            130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
            275                 280                 285

Gly Ser Ile Arg Ser Pro His Leu Met Asp Ile Leu Asn Ser Ile Thr
290                 295                 300

Ile Tyr Thr Asp Ala His Lys Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Thr Phe Ser Trp Gln His Arg Ser Ala Glu Phe Asn Asn
450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
```

-continued

```
                500                 505                 510
Val Asn Ile Thr Ala Pro Leu Ser Gln Arg Tyr Arg Val Arg Ile Arg
                515                 520                 525

Tyr Ala Ser Thr Thr Asn Leu Gln Phe His Thr Ser Ile Asp Gly Arg
            530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
            595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
            645                 650                 655

Asp Glu Phe Cys Leu Asp Glu Lys Gln Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
    690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
            755                 760                 765

Asn Ala Lys His Glu Thr Val Asn Val Pro Gly Thr Gly Ser Leu Trp
770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
            805                 810                 815

Asp Gly Glu Lys Cys Ala His His Ser His His Phe Ser Leu Asp Ile
        820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Arg Leu Gly Asn Leu Glu
    850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
            885                 890                 895

Thr Asn Ile Val Tyr Lys Glu Ala Lys Glu Ser Val Asp Ala Leu Phe
            900                 905                 910

Val Asn Ser Gln Tyr Asp Gln Leu Gln Ala Asp Thr Asn Ile Ala Met
        915                 920                 925
```

```
Ile His Ala Ala Asp Lys Arg Val His Ser Ile Arg Glu Ala Tyr Leu
    930              935              940

Pro Glu Leu Ser Val Ile Pro Gly Val Asn Ala Ala Ile Phe Glu Glu
945              950              955              960

Leu Glu Gly Arg Ile Phe Thr Ala Phe Ser Leu Tyr Asp Ala Arg Asn
                965              970              975

Val Ile Lys Asn Gly Asp Phe Asn Asn Gly Leu Ser Cys Trp Asn Val
            980              985              990

Lys Gly His Val Asp Val Glu Glu Gln Asn Asn Gln Arg Ser Val Leu
        995              1000             1005

Val Leu Pro Glu Trp Glu Ala Glu Val Ser Gln Glu Val Arg Val Cys
    1010             1015             1020

Pro Gly Arg Gly Tyr Ile Leu Arg Val Thr Ala Tyr Lys Glu Gly Tyr
1025             1030             1035             1040

Gly Glu Gly Cys Val Thr Ile His Glu Ile Glu Asn Asn Thr Asp Glu
                1045             1050             1055

Leu Lys Phe Ser Asn Cys Val Glu Glu Ile Tyr Pro Asn Asn Thr
            1060             1065             1070

Val Thr Cys Asn Asp Tyr Thr Val Asn Gln Glu Glu Tyr Gly Gly Ala
        1075             1080             1085

Tyr Thr Ser Arg Asn Arg Gly Tyr Asn Glu Ala Pro Ser Val Pro Ala
    1090             1095             1100

Asp Tyr Ala Ser Val Tyr Glu Glu Lys Ser Tyr Thr Asp Gly Arg Arg
1105             1110             1115             1120

Glu Asn Pro Cys Glu Phe Asn Arg Gly Tyr Arg Asp Tyr Thr Pro Leu
            1125             1130             1135

Pro Val Gly Tyr Val Thr Lys Glu Leu Glu Tyr Phe Pro Glu Thr Asp
            1140             1145             1150

Lys Val Trp Ile Glu Ile Gly Glu Thr Glu Gly Thr Phe Ile Val Asp
        1155             1160             1165

Ser Val Glu Leu Leu Leu Met Glu Glu
    1170             1175
```

PROCESS FOR ALTERING THE HOST RANGE OR INCREASING THE TOXICITY OF *BACILLUS THURINGIENSIS* LEPIDOTERAN TOXINS, AND RECOMBINANT DNA SEQUENCES THEREFOR

CROSS REFERENCE TO A RELATED APPLICATION

This is a continuation of application Ser. No. 08/580,781, filed on Dec. 29, 1995, now abandoned; which is a continuation of application Ser. No. 08/420,615, filed on Apr. 10, 1995, now abandoned; which is a continuation of application Ser. No. 08/097,808, filed on Jul. 27, 1993, now abandoned; which is a divisional of application Ser. No. 07/980,128, filed on Nov. 23, 1992, now abandoned; which is a continuation of application Ser. No. 07/803,920, filed on Dec. 6, 1991, now abandoned; which is a continuation of application Ser. No. 07/356,599, filed on May 24, 1989, now abandoned; which is a continuation of application Ser. No. 06/904,572, filed on Sep. 5, 1986, now abandoned; which is a continuation-in-part of application Ser. No. 06/808,129, filed on Dec. 12, 1985, now abandoned.

BACKGROUND OF THE INVENTION

The most widely used microbial pesticides are derived from the bacterium *Bacillus thuringiensis*. This bacterial agent is used to control a wide range of leaf-eating caterpillars, Japanese beetles and mosquitos. *Bacillus thuringiensis* produces a proteinaceous paraspore or crystal which is toxic upon ingestion by a susceptible insect host. For example, *B. thuringiensis* var. *kurstaki* HD-1 produces a crystal called a delta toxin which is toxic to the larvae of a number of lepidopteran insects. The cloning and expression of this B.t. crystal protein gene in *Escherichia coli* has been described in the published literature (Schnepf, H. E. and Whiteley, H. R. [1981] Proc. Natl. Acad. Sci. USA 78:2893–2897). U.S. Pat. No. 4,448,885 and U.S. Pat. No. 4,467,036 both disclose the expression of B.t. crystal protein in *E. coli*. In U.S. Pat. No. 4,467,036 *B. thuringiensis* var. *kurstaki* HD-1 is disclosed as being available from the well-known NRRL culture repository at Peoria, Ill. Its accession number there is NRRL B-3792. *B. thuringiensis* var. *kurstaki* HD-73 is also available from NRRL. Its accession number is NRRL B-4488.

SUMMARY OF THE INVENTION

The subject invention concerns a novel process for altering the insect host range of *Bacillus thuringiensis* toxins, and novel toxins produced as exemplification of this useful process. This alteration can result in expansion of the insect host range of the toxin, and/or amplification of host toxicity. The process comprises recombining in vitro the variable region(s) of two or more δ-endotoxin genes. Specifically exemplified is the recombining of portions of two *Bacillus thuringiensis* var. *kurstaki* DNA sequences, i.e., referred to herein as k-1 and k-73, to produce chimeric B.t. toxins with expanded host ranges as compared to the toxins produced by the parent DNA's.

"Variable regions," used herein, refers to the non-homologous regions of two or more DNA sequences. As shown by the examples presented herein, the recombining of such variable regions from two different B.t. DNA sequences yields, unexpectedly, a DNA sequence encoding a δ-endotoxin with an expanded insect host range. In a related example, the recombining of two variable regions of two different B.t. toxin genes results in the creation of a chimeric toxin molecule with increased toxicity toward the target insect. The utility of this discovery by the inventors is clearly broader than the examples disclosed herein. From this discovery, it can be expected that a large number of new and useful toxins will be produced. Thus, though the subject process is exemplified by construction of chimeric toxin-producing DNA sequences from two well-known B.t. *kurstaki* DNA sequences, it should be understood that the process is not limited to these starting DNA sequences. The invention process also can be used to construct chimeric toxins from any *B. thuringiensis* toxin-producing DNA sequence.

BRIEF DESCRIPTION OF THE SEQUENCES

Figure 1:
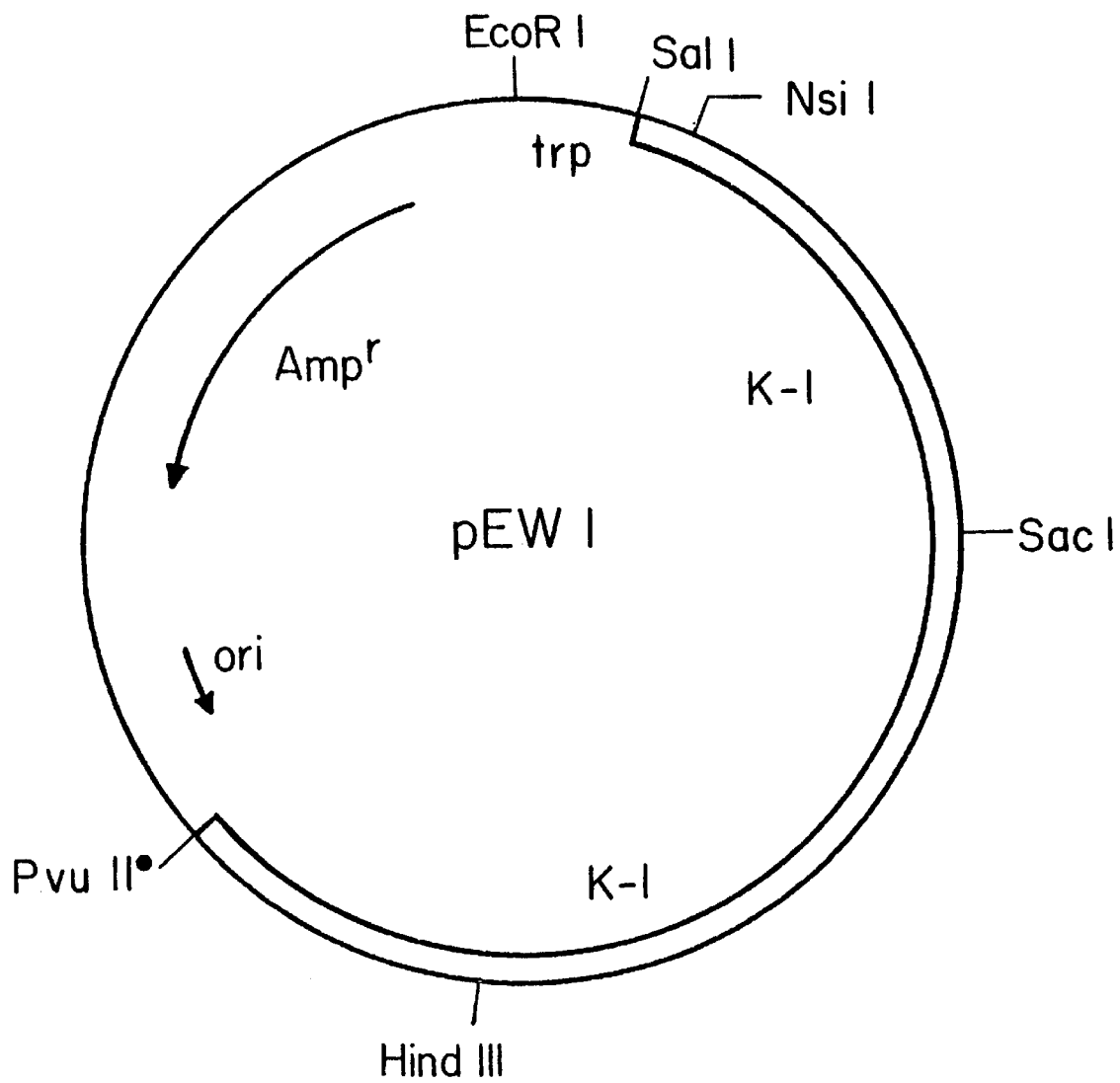
FIG. 1: A schematic diagram of plasmid pEW1 which contains the DNA sequence encoding *Bacillus thuringiensis* toxin k-1.

SEQ ID NO. 1 is the nucleotide sequence of plasmid pEW3 encoding the chimeric toxin.

SEQ ID NO. 2 is the deduced amino acid sequence of the chimeric toxin encoded by the nucleotide sequence of SEQ ID NO: 1.

SEQ ID NO. 3 is the nucleotide sequence of plasmid pEW4 encoding the chimeric toxin.

SEQ ID NO. 4 is the deduced amino acid sequence of the chimeric toxin encoded by the nucleotide sequence of SEQ ID NO: 3.

SEQ ID NO. 5 is the nucleotide sequence of plasmid pACB-1 encoding the chimeric toxin ACB-1.

SEQ ID NO. 6 is the deduced amino acid sequence of the chimeric toxin encoded by the nucleotide sequence of SEQ ID NO: 5.

SEQ ID NO. 7 is the nucleotide sequence of plasmid pSYW1 encoding chimeric toxin SYW1.

SEQ ID NO. 8 is the deduced amino acid sequence of the chimeric toxin encoded by the nucleotide sequence of SEQ ID NO: 7.

DETAILED DESCRIPTION OF THE INVENTION

Upon recombining in vitro the variable region(s) of two or more δ-endotoxin genes, there is obtained a gene(s) encoding a chimeric toxin(s) which has an expanded and/or amplified host toxicity as compared to the toxin produced by the starting genes. This recombination is done using standard well-known genetic engineering techniques.

The restriction enzymes disclosed herein can be purchased from Bethesda Research Laboratories, Gaithersburg, Md., or New England Biolabs, Beverly, Ma. The enzymes are used according to the instructions provided by the supplier.

The various methods employed in the preparation of the plasmids and transformation of host organisms are well known in the art. These procedures are all described in Maniatis, T., Fritsch, E. F., and Sambrook, J. (1982) *Molecular Cloning: A Laboratory Manual,* Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

Plasmids pEW1, pEW2, pEW3, and pEW4, constructed as described infra, have been deposited in *E. coli* hosts in the permanent collection (to be maintained for at least 30 years) of the Northern Regional Research Laboratory (NRRL), U.S. Department of Agriculture, Peoria, Ill., USA. Their accession numbers and dates of deposit are as follows:

pEW1—NRRL B-18032; deposited on Nov. 29, 1985
pEW2—NRRL B-18033; deposited on Nov. 29, 1985
pEW3—NRRL B-18034; deposited on Nov. 29, 1985
pEW4—NRRL B-18035; deposited on Nov. 29, 1985

*B. thuringiensis* strain MTX-36, NRRL B-18101 was deposited on Aug. 25, 1986.

Plasmid pBR322 is a well-known and available plasmid. It is maintained in the *E. coli* host ATCC 37017. Purified pBR322 DNA can be obtained as described in Bolivar, F., Rodriguez, R. L., Greene, P. J., Betlach, M. C., Heynecker, H. L., Boyer, H. W., Crosa, J. H. and Falkow, S. (1977) Gene 2:95–113; and Sutcliffe, J. G. (1978) Nucleic Acids Res. 5:2721–2728.

NRRL B-18032, NRRL B-18033, NRRL B-18034, NRRL B-18035, and NRRL B-18101 are available to the public upon the grant of a patent which discloses these accession numbers in conjunction with the invention described herein. It should be understood that the availability of these deposits does not constitute a license to practice the subject invention in derogation of patent rights granted for the subject invention by governmental action.

As disclosed above, any *B. thuringiensis* toxin-producing DNA sequence can be used as starting material for the subject invention. Examples of *B. thuringiensis* organisms, other than those previously given, are as follows:

*Bacillus thuringiensis* var. *israelensis*—ATCC 35646
*Bacillus thuringiensis* M-7—NRRL B-15939
*Bacillus thuringiensis* var. *tenebrionis*—DSM 2803

The following *B. thuringiensis* cultures are available from the United States Department of Agriculture (USDA) at Brownsville, Tex. Requests should be made to Joe Garcia, USDA, ARS, Cotton Insects Research Unit, P.O. Box 1033, Brownsville, Tex. 78520 USA.

*B. thuringiensis* HD2
*B. thuringiensis* var. *finitimus* HD3
*B. thuringiensis* var. *alesti* HD4
*B. thuringiensis* var. *kursatki* HD73
*B. thuringiensis* var. *sotto* HD770
*B. thuringiensis* var. *dendrolimus* HD7
*B. thuringiensis* var. *kenyae* HD5
*B. thuringiensis* var. *galleriae* HD29
*B. thuringiensis* var. *canadensis* HD224
*B. thuringiensis* var. *entomocidus* HD9
*B. thuringiensis* var. *subtoxicus* HD109
*B. thuringiensis* var. *aizawai* HD11
*B. thuringiensis* var. *morrisoni* HD12
*B. thuringiensis* var. *ostriniae* HD501
*B. thuringiensis* var. *tolworthi* HD537
*B. thuringiensis* var. *darmstadiensis* HD146
*B. thuringiensis* var. *toumanoffi* HD201
*B. thuringiensis* var. *kyushuensis* HD541
*B. thuringiensis* var. *thompsoni* HD542
*B. thuringiensis* var. *pakistani* HD395
*B. thuringiensis* var. *israelensis* HD567
*B. thuringiensis* var. *indiana* HD521
*B. thuringiensis* var. *dakota*
*B. thuringiensis* var. *tohokuensis* HD866
*B. thuringiensis* var. *kumanotoensis* HD867
*B. thuringiensis* var. *tochigiensis* HD868
*B. thuringiensis* var. *colmeri* HD847
*B. thuringiensis* var. *wuhanensis* HD525

Though the main thrust of the subject invention is directed toward a process for altering the host range of *B. thuringiensis* toxins, the process is also applicable in the same sense to other Bacillus toxin-producing microbes. Examples of such Bacillus organisms which can be used as starting material are as follows:

*Bacillus cereus*—ATCC 21281
*Bacillus moritai*—ATCC 21282
*Bacillus popilliae*—ATCC 14706
*Bacillus lentimorbus*—ATCC 14707
*Bacillus sphaericus*—ATCC 33203

*Bacillus thuringiensis* M-7, exemplified herein, is a *Bacillus thuringiensis* isolate which, surprisingly, has activity against beetles of the order Coleoptera but not against *Trichoplusia ni, Spodoptera exigua* or *Aedes aegypti*. Included in the Coleoptera are various Diabrotica species (family Chrysomelidae) that are responsible for large agricultural losses, for example, *D. undecimpuctata* (western spotted cucumber beetle), *D. longicornis* (northern corn rootworm), *D. virgitera* (western corn rootworm), and *D. undecimpunctata howardi* (southern corn rootworm).

*B. thuringiensis* M-7 is unusual in having a unique parasporal body (crystal) which under phase contrast microscopy is dark in appearance with a flat, square configuration.

The pesticide encoded by the DNA sequence used as starting material for the invention process can be any toxin produced by a microbe. For example, it can be a polypeptide which has toxic activity toward a eukaryotic multicellular pest, such as insects, e.g., coleoptera, lepidoptera, diptera, hemiptera, dermaptera, and orthoptera; or arachnids; gastropods; or worms, such as nematodes and platyhelminths. Various susceptible insects include beetles, moths, flies, grasshoppers, lice, and earwigs.

Further, it can be a polypeptide produced in active form or a precursor or proform requiring further processing for toxin activity, e.g., the novel crystal toxin of *B. thuringiensis* var. *kurstaki,* which requires processing by the pest.

The constructs produced by the process of the invention, containing chimeric toxin-producing DNA sequences, can be transformed into suitable hosts by using standard procedures, Illustrative host cells may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and lower eukaryotes, such as fungi. Illustrative prokaryotes, both Gram-negative and -positive, include Enerobacteriaceae, such as Escherichia, Erwinia, Shigella, Salmonella, and Proteus; Bacillaceae; Rhizobiaceae, such as Rhizobrium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the chimeric toxin-producing gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other consideration include ease of formulation and handling, economics, storage stability, and the like.

Host organisms of particular interest include yeast, such as Rhodotorula sp., Aeurobasidium sp., Saccharomyces sp., and Sporobolomyces sp.; phylloplane organisms such Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis,* and the like.

The chimeric toxin-producing gene(s) can be introduced into the host in any convenient manner, either providing for extrachromosomal maintenance or integration into the host game.

Various constructs may be used, which include replication systems from plasmids, viruses, or centromeres in combination with an autonomous replicating segment (ars) for stable maintenance. Where only integration is desired, constructs can be used which may provide for replication, and are either transposons or have transposon-like insertion activity or provide for homology with the genome of the host. DNA sequences can be employed having the chimeric toxin-producing gene between sequences which are homologous with sequences in the genome of the host, either chromosomal or plasmid. Desirably, the chimeric toxin-producing gene(s) will be present in multiple copies. See for example, U.S. Pat. No. 4,399,216. Thus, conjugation, transduction, transfection and transformation may be employed for introduction of the gene.

A large number of vectors are presently available which depend upon eukaryotic and prokaryotic replication systems, such as ColEl, P-1 incompatibility plasmids, e.g., pRK290, yeast 2m $\mu$ plasmid, lembda, and the like.

Where an extrachromosomal element is employed, the DNA construct will desirably include a marker which allows for a selection of those host cells containing the construct. The marker is commonly one which provides for biocide resistance, e.g., antibiotic resistance or heavy metal resistance, complementation providing prototrophy to an auxotrophic host, or the like. The replication systems can provide special properties, such as runaway replication, can involve cos cells, or other special feature.

Where the chimeric toxin-producing gene(s) has transcriptional and translational initiation and termination regulatory signals recognized by the host cell, it will frequently be satisfactory to employ those regulatory features in conjunction with the gene. However, in those situations where the chimeric toxin-producing gene is modified, as for example, removing a leader sequence or providing a sequence which codes for the mature form of the pesticide, where the entire gene encodes for a precursor, it will frequently be necessary to manipulate the DNA sequence, so that a transcriptional initiation regulatory sequence may be provided which is different from the natural one.

A wide variety of transcriptional initiation sequences exist for a wide variety of hosts. The sequence can provide for constitutive expression of the pesticide or regulated expression, where the regulation may be inducible by a chemical, e.g., a metabolite, by temperature, or by a regulatable repressor. See for example, U.S. Pat. No. 4,374,927. The particular choice of the promoter will depend on a number of factors, the strength of the promoter, the interference of the promoter with the viability of the cells, the effect of regulatory mechanisms endogenous to the cell on the promoter, and the like. A large number of promoters are available from a variety of sources, including commercial sources.

The cellular host containing the chimeric toxin-producing pesticidal gene may be grown in any convenient nutrient medium, where the DNA construct provides a selective advantage, providing for a selective medium so that substantially all or all of the cells retain the chimeric toxin-producing gene. These cells may then be harvested in accordance with conventional ways and modified in the various manners described above. Alternatively, the cells can be fixed prior to harvesting.

Host cells transformed to contain chimeric toxin-producing DNA sequences can be treated to prolong pesticidal activity when the cells are applied to the environment of a target pest. This treatment can involve the killing of the host cells under protease deactivating or cell wall strengthening conditions, while retaining pesticidal activity.

The cells may be inhibited from proliferation in a variety of ways, so long as the technique does not deleteriously affect the properties of the pesticide, nor diminish the cellular capability in protecting the pesticide. The techniques may involve physical treatment, chemical treatment, changing the physical character of the cell or leaving the physical character of the cell substantially intact, or the like.

Various techniques for inactivating the host cells include heat, usually 50° C. to 70° C.; freezing; UV irradiation; lyophilization; toxins, e.g., antibiotics; phenols; anilides, e.g., carbanilide and salicylanilide; hydroxyurea; quaternaries; alcohols, antibacterial dyes; EDTA and amidines; non-specific organic and inorganic chemicals, such as halogenating agents, e.g., chlorinating, brominating or iodinating agents; aldehydes, e.g., glutaraldehyde or formaldehyde; toxic gases, such as ozone and ethylene oxide; peroxide; psoralens; desiccating agents; or the like, which may be used individually or in combination. The choice of agent will depend upon the particular pesticide, the nature of the host cell, the nature of the modification of the cellular structure, such as fixing and preserving the cell wall with crosslinking agents, or the like.

The cells generally will have enhanced structural stability which will enhance resistance to environmental degradation in the field. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bioavailability or bioactivity of the toxin.

The method of treating the organism can fulfill a number of functions. First, it may enhance structural integrity. Second, it may provide for enhanced proteolytic stability of the toxin, by modifying the toxin so as to reduce its susceptibility to proteolytic degradation and/or by reducing the proteolytic activity of proteases naturally present in the cell. The cells are preferably modified at an intact stage and when there has been a substantial build-up of the toxin protein. These modifications can be achieved in a variety of ways, such as by using chemical reagents having a broad spectrum of chemical reactivity. The intact cells can be combined with a liquid reagent medium containing the chemical reagents, with or without agitation at temperatures in the range of about −10 to 60° C. The reaction time may be determined empirically and will vary widely with the reagents and reaction conditions. Cell concentrations will vary form about 10E2 to 10E10 per ml.

Of particular interest as chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W.H. Freeman and Company, 1967); or a combination of physical (heat) and chemical agents that prolong the activity of the toxin produced in the cell when the cell is applied to the environment of the target pest(s).

For halogenation with iodine, temperatures will generally range from about 0 to 50° C., but the reaction can be conveniently carried out at room temperature. Conveniently, the iodination may be performed using triiodide or iodine at 0.5 to 5% in an acidic aqueous medium, particularly an aqueous carboxylic acid solution that may vary from about 0.5–5M. Conveniently, acetic acid may be used, although other carboxylic acids, generally of from about 1 to 4 carbon atoms, may also be employed. The time for the reaction will generally range from less than a minute to about 24 hrs, usually from about 1 to 6 hrs. Any residual iodine may be removed by reaction with a reducing agent, such as dithionite, sodium thiosulfate, or other reducing agent compatible with ultimate usage in the field. In addition, the modified cells may be subjected to further treatment, such as washing to remove all of the reaction medium, isolation in dry form, and formulation with typical stickers, spreaders, and adjuvants generally utilized in agricultural applications, as is well known to those skilled in the art.

Of particular interest are reagents capable of crosslinking the cell wall. A number of reagents are known in the art for this purpose. The treatment should result in enhanced stability of the pesticide. That is, there should be enhanced persistence or residual activity of the pesticide under field conditions. Thus, under conditions where the pesticidal activity of untreated cells diminishes, the activity of treated cells remains for periods of from 1 to 3 times longer.

The cells can be formulated for use in the environment in a variety of ways. They can be employed as wettable powders, granules, or dusts, by mixing with various inert materials, such as inorganic minerals (phyllosilicates, carbonates, sulfates, or phosphates) or botanical materials (powdered corncobs, rice hulls, or walnut shells). The formulations can include spreader/sticker adjuvants, stabilizing agents, other pesticidal additives, or surfactants. Liquid formulations can be aqueous-based or non-aqueous and employed as foams, gels, suspensions, emulsifiable concentrates, and the like. The ingredients can include rheological agents, surfactants, emulsifiers, dispersants, polymers, and the like.

The pesticidal concentration will vary depending upon the nature of the particular formulation, e.g., whether it is a concentrate or to be used undiluted. The pesticide will generally be present at a concentration of at least about 1% by weight, but can be up to 100% by weight. The dry formulations will have from about 1 to 95% by weight of the pesticide, while the liquid formulations will generally be from about 1 to 60% by weight of the solids in the liquid phase. The formulations will generally have from about 1E2 to 1E8 cells/mg.

The formulations can be applied to the environment of the pest(s), e.g., plants, soil or water, by spraying, dusting, sprinkling, or the like. These formulations can be administered at about 2 oz (liquid or dry) to 2 or more pounds per hectare, as required.

Following are examples which illustrate procedures, including the best mode, for practicing the invention. These examples should not be construed as limiting. All percentages are by weight and all solvent mixture proportions are by volume unless otherwise noted.

EXAMPLE 1

Construction of plasmid pEW1

The k-1 gene is the hd-1 gene described by Schnepf et al. (J. Biol. Chem. 260:6264–6272 1985). The k-1 gene was resected from the 5' end with Bal31 up to position 54. To this position was added a SalI linker (5'GTCCGACC3'). The 3' end of the gene was cleaved at position 4211 with the enzyme NdeI and blunt ended with the Klenow fragment of DNA polymerase.

The cloning vector pUC8 (Messing, J. and Vieira, J. [1982] Gene 19:269–276) which can be purchased from Pharmacia, Piscataway, N.J., was cleaved with SalI and EcoRI and cloned into plasmid pBR322 which had been cut with the same enzymes. The trp promoter (Genblock, available from Pharmacia) was blunt ended at the 5' end with Klenow and inserted into this hybrid vector by blunt end ligation of the 5' end to the SmaI site of the vector, and by insertion of the 3' end at the SalI site of the vector. The k-1 gene was then inserted using the SalI site at the 5' end and by blunt end ligation of the 3' end to the PvuII site of the vector. A schematic drawing of this construct, called pEW1, is shown in FIG. 1 of the drawings.

Plasmid pEW1 contains the DNA sequence encoding *Bacillus thuringiensis* toxin k-1.

EXAMPLE 2

Construction of plasmid pEW2

The k-73 gene is the HD-73 gene described by Adang et al. (Gene 36:289–300 1985). The k-73 gene was cleaved at position 176 with NsiI. The sequence was then cleaved at position 3212 with HindIII and the 3036 base fragment consisting of residues 176–3212 was isolated by agarose gel electrophoresis.

Figure 2:
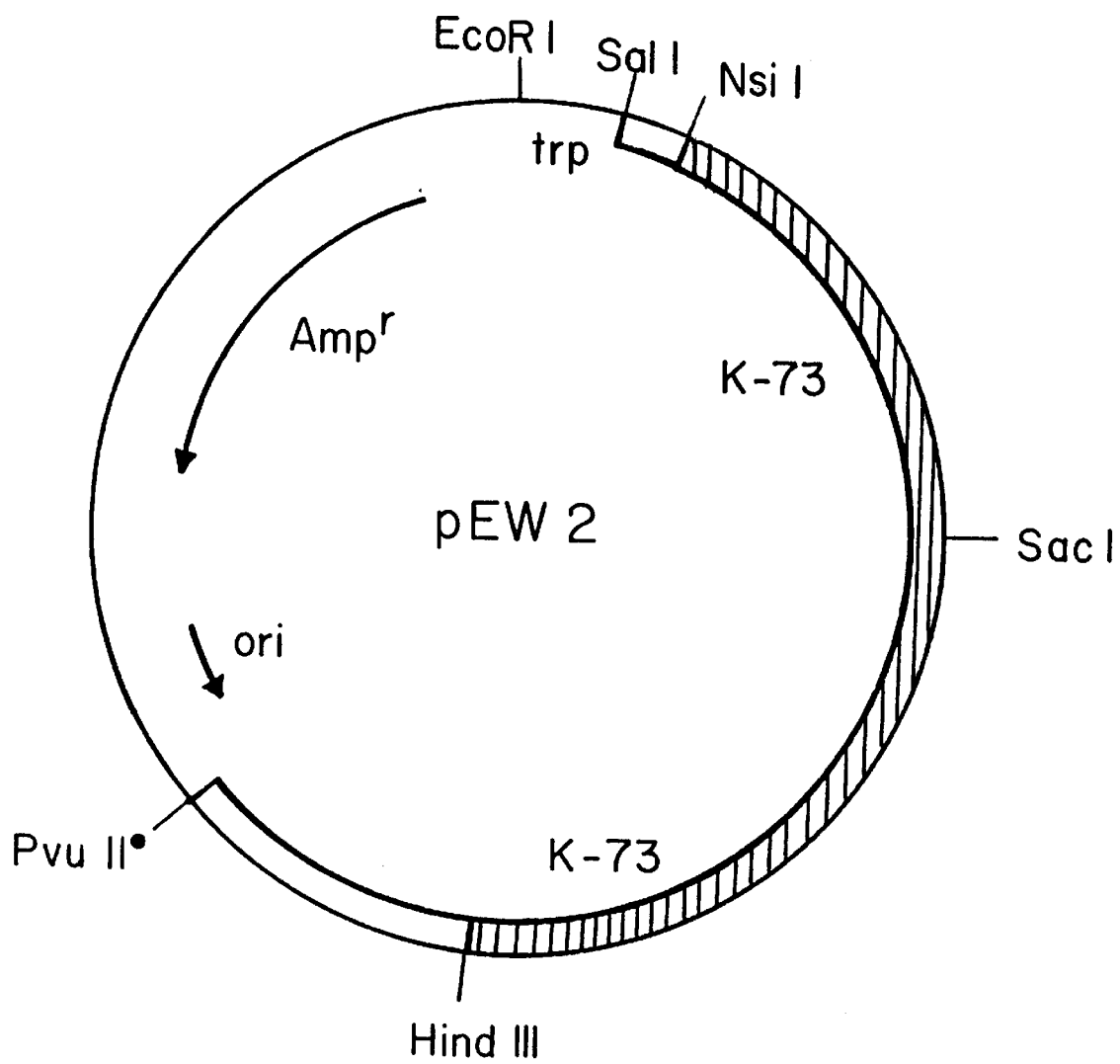
FIG. 2: A schematic diagram of plasmid pEW2 which contains the DNA sequence encoding *Bacillus thuringiensis* toxin k-73.

Plasmid pEW1, prepared as described in Example 1, was also cleaved with HindIII (position 33456 in Table 1, SEQ ID NO:1) and partially digested with NsiI (position 556 in Table 1, SEQ ID NO:1). The 3036 base fragment from k-73, disclosed above, was inserted into the NsiI to HindIII region of pEW1 replacing the comparable fragment of the k-1 gene, and creating plasmid pEW2. A schematic diagram of pEW2 is shown in FIG. 2 of the drawings.

Plasmid pEW2 contains the DNA sequence encoding *Bacillus thuringiensis* toxin k-73.

EXAMPLE 3

Construction of plasmid pEW3

The k-1 gene was cut with SacI at position 1873.

Figure 3:
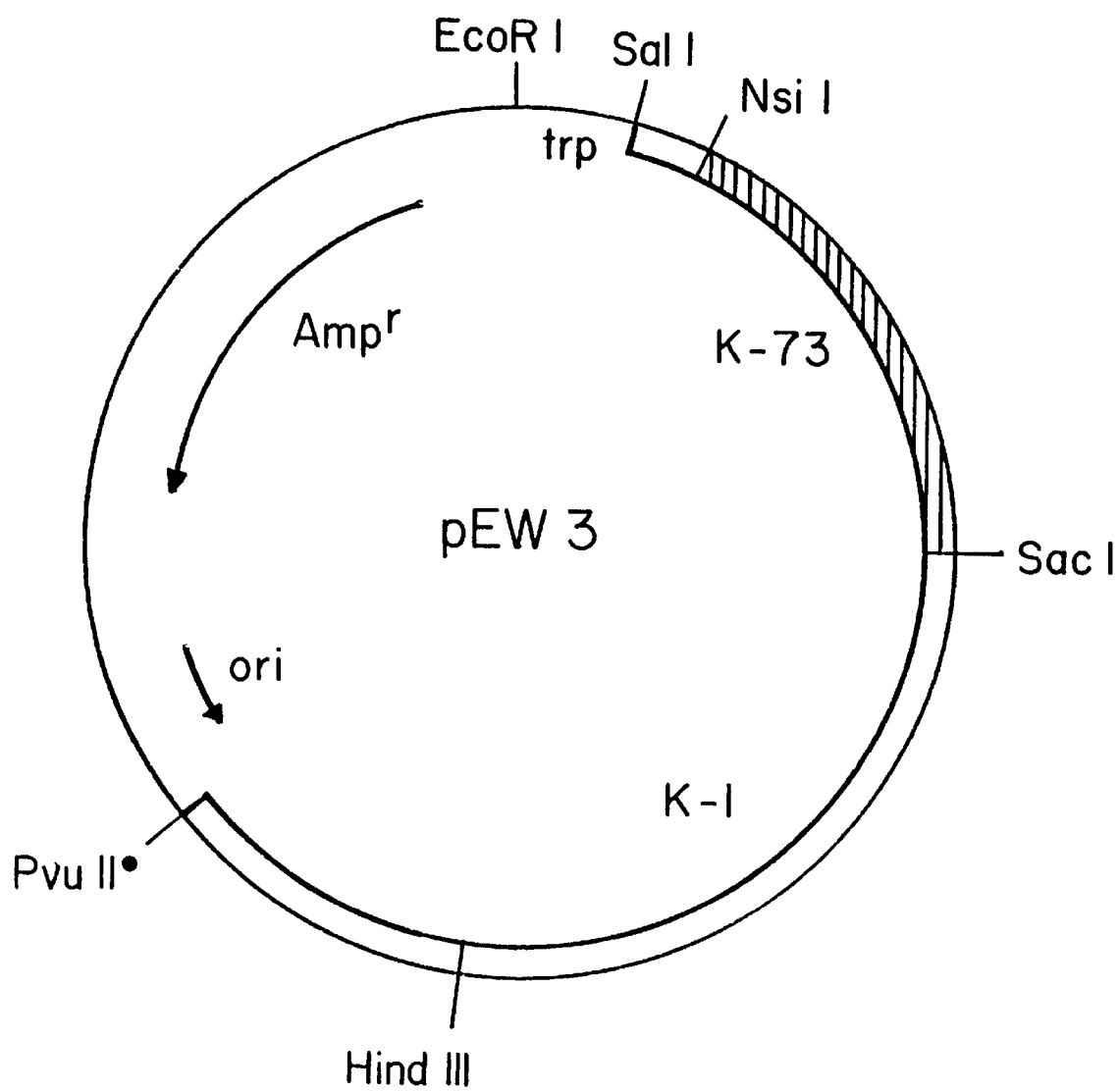
FIG. 3: A schematic diagram of plasmid pEW3 which contains the DNA sequence encoding *Bacillus thuringiensis* chimeric toxin k-73/k-1 (pHY).

The gene was then submitted to partial digestion with HindIII and the 1427 base fragment consisting of residues 1873 to 3345 was isolated by agarose gel electrophoresis. Plasmid pEW2 was cut with SacI and HindIII and the large fragment representing the entire plasmid minus the SacI to HindIII fragment of the k-73 gene was isolated by agarose gel electrophoresis. The 1427 base fragment from the k-1 gene was then ligated into the SacI to HindIII region of pEW2, creating plasmid pEW3. A schematic diagram of pEW3 is shown in FIG. 3 of the drawings.

Plasmid pEW3 contains the DNA sequence encoding *Bacillus thuringiensis* chimeric toxin k-73/k-1 (pHY).

The nucleotide sequence encoding the chimeric toxin is shown in Table 1 (SEQ ID NO:1). The deduced amino acid sequence is shown in Table 1A (SEQ ID NO:2).

EXAMPLE 4

Construction of plasmid pEW4

Figure 4:
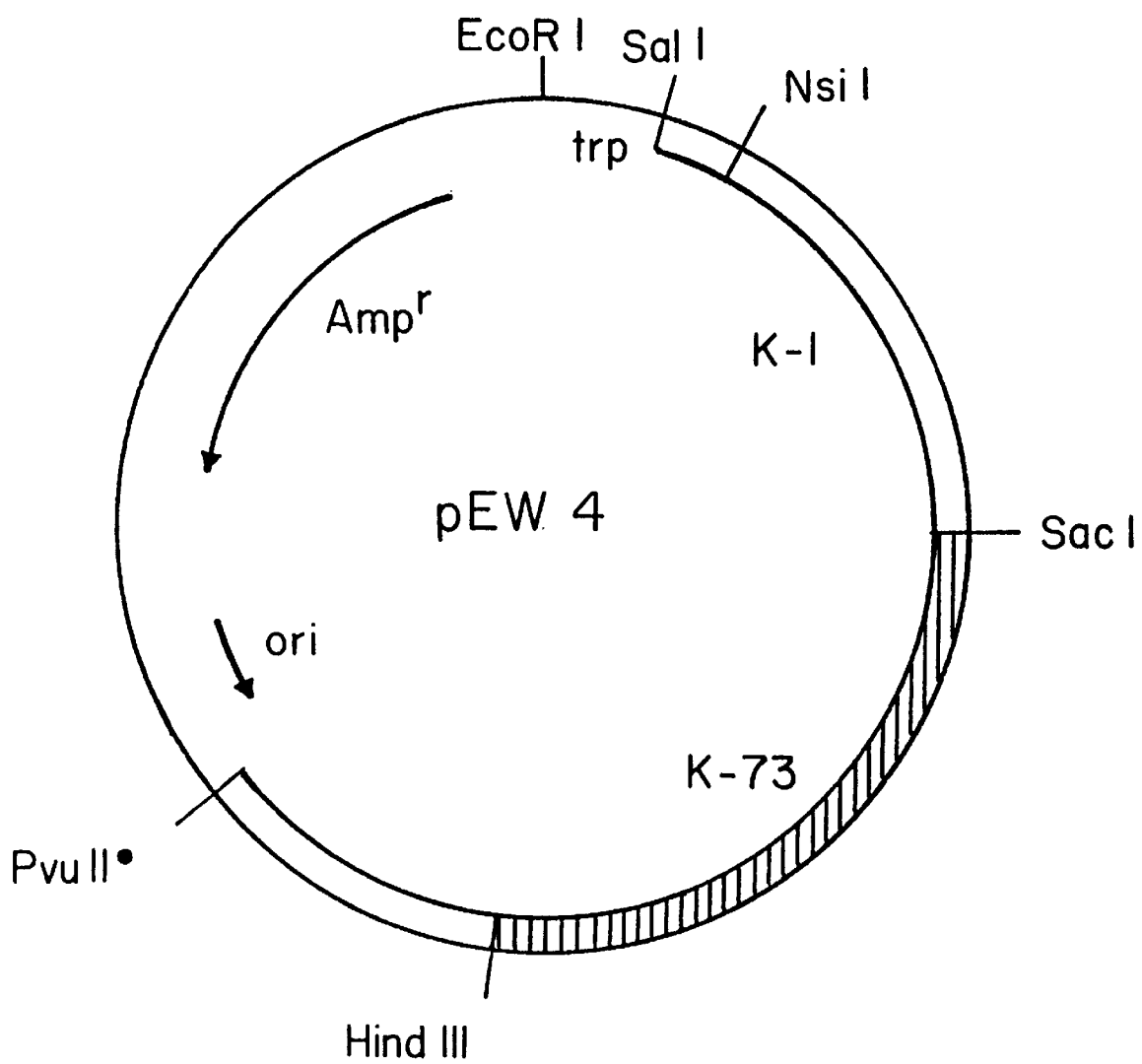
FIG. 4: A schematic diagram of plasmid pEW4 which contains the DNA sequence encoding *Bacillus thuringiensis* chimeric toxin k-1/k-73 (pYH).

The k-1 gene was cut at position 556 with NsiI. The gene was then cut with SacI at position 1873 and the 1317 base fragment from NsiI to SacI was isolated by agarose gel electrophoresis. Plasmid pEW2 was cut with SacI and then submitted to partial digestion with NsiI. The large fragment representing the entire plasmid, minus the NsiI to SacI region of the k-73 gene, was isolated by agarose gel electrophoresis. The 1317 base NsiI to SacI fragment of gene k-1 was then ligated into NsiI to SacI region of pEW2 to create plasmid pEW4. A schematic diagram of pEW4 is shown in FIG. 4 of the drawings.

The nucleotide sequence encoding the chimeric toxin is shown in Table 2 (SEQ ID NO:3). The deduced amino acid sequence is shown in Table 2A (SEQ ID NO:4).

Plasmid pEW4 contains the DNA sequence encoding *Bacillus thuringiensis* chimeric toxin k-1/k-73 (PYH).

EXAMPLE 5

Insertion of Chimeric Toxin Genes Into Plants

Genes coding for chimeric insecticidal toxins, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J. [1983] EMBO J. 2:2143–2150; Bartok, K., Binns, A., Matzke, A. and Chilton, M. D. [1983] Cell 32:1033–1043). A particularly useful vector in this regard is pEND4K (Klee, H. J., Yanofsky, M. F. and Nester, E. W. [1985] Bio/Technology 3:637–642). This plasmid can replicate both in plant cells and in bacteria and has multiple cloning sites for passenger genes. Toxin genes, for example, can be inserted into the BamHI site of pEND4K, propagated in *E. coli*, and transformed into appropriate plant cells.

EXAMPLE 6

Cloning of *B. thuringiensis* genes into baculoviruses

Genes coding for *Bacillus thuringiensis* Chimeric toxins, as disclosed herein, can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol. Cell. Biol. 3:2156–2165). The genes coding for k-1, k-73, k-73/k-1, k-1/k-73, or other B.t. genes can be modified with BamHI linkers at appropriate regions both upstream and downstream from the coding regions and inserted into the passenger site of one of the AcNPV vectors.

EXAMPLE 7

Chimeric Toxin Denoted ACB-1

Enhanced toxicity against all three insects tested was shown by a toxin denoted ACB-1. The toxin ACB-1 (Table 3A, SEQ ID NO:6) is encoded by plasmid pACB-1 (Table 3, SEQ ID NO:5). The insecticidal activity encoded by pACB-1, in comparison with pEW3 (Example 3), is as follows:

| Clone | LC$_{50}$ (O.D.$_{575}$/ml) | | |
|---|---|---|---|
| | T. ni | H. zea | S. exigua |
| pEW3 | 4.3 | 23.0 | 12.3 |
| pACB-1 | 1.2 | 3.9 | 1.2 |

The above test was conducted using the conditions described previously.

The above results show that the ACB-1 toxin has the best composite activity as compared to the other toxins tested herein against all three insects.

Plasmid pACB-1 was constructed between the variable region of MTX-36, a wild *B. thuringiensis* strain, having the deposit accession number NRRL B-18101, and the variable region of HD-73 as follows: MTX-36; N-terminal to SacI site. HD-73; SacI site to C-terminal.

Total plasmid DNA was prepared from strain MTX-36 by standard procedures. The DNA was submitted to complete digestion by restriction enzymes SpeI and DraI. The digest was separated according to size by agarose gel electrophoresis and a 1962 bp fragment was purified by electroelution using standard procedures.

Plasmid pEW3 was purified and digested completely with SpeI and then submitted to partial digestion with DraI. The digest was submitted to agarose gel electrophoresis and a 4,138 bp fragment was purified by electroelution as above.

The two fragments (1962 bp from MTX-36 and 4138 bp from pEW3 were ligated together to form construct pACB.

Plasmid DNA was prepared from pACB, digested completely with SacI and NdeI and a 3760 bp fragment was isolated by electroelution following agarose gel electrophoresis.

Plasmid pEW1 was digested completely with SacI and NdeI and a 2340 bp fragment was isolated by electroelution following agarose gel electrophoresis.

The two fragments (3760 bp from pACB and 2340 from pEW1) were ligated together to form construct pACB-1.

The complete nucleotide sequence of the ACB-1 gene was determined and the deduced amino acid sequence of the toxin was compared with that determined for the toxin encoded by pEW3 (EW3). The result was that the deduced amino acid sequence of the ACB-1 toxin was identical to that of EW3 with two exceptions: (1) Aspartic acid residue 411 in EW3 was changed to asparagine in ACB-1 and (2) glycine residue 425 in EW3 was changed to glutamic acid in ACB-1. These two amino acid changes account for all of the changes in insect toxicity between these strains. The amino acid sequence of the EW3 toxin is as reported in Table 1 (SEQ ID NO:1). A schematic representation of these two toxins is as follows:

```
    NH2                 NH2
     |                   |
     |                   |
    411-Asp  ———▶  411-Asn
     |                   |
    411-Gly  ———▶  425-Glu
     |                   |
     |                   |
    COOH               COOH
    EW3                ACB-1
```

The above disclosure is further exemplification of the subject invention process for altering the host range of Bacillus toxins which comprises recombining in vitro the variable region of two or more toxin genes. Once a chimeric toxin is produced, the gene encoding the same can be sequenced by standard procedures, as disclosed above. The sequencing data can be used to alter other DNA by known molecular biology procedures to obtain the desired novel toxin. For example, the above-noted changes in the ACB-1 gene from HD-73, makes it possible to construct the ACB-1 gene as follows:

Plasmid pEW3, NRRL B-18034, was modified by altering the coding sequence for the toxin. The 151 bp DNA fragment bounded by the AccI restriction site at nucleotide residue 1199 in the coding sequence, and the SacI restriction site at residue 1350 were removed by digestion with the indicated restriction endonucleases using standard procedures. The removed 151 bp DNA fragment was replaced with the following synthetic DNA oligomer by standard procedures:

A TAC AGA AAA AGC GGA ACG GTA GAT TCG CTG
  AAT GAA ATA CCG CCA CAG AAT AAC AAC GTG
  CCC CCG AGG CAA GAA TTT AGT CAT CGA TTA
  AGC CAT GTT TCA ATG TTT AGA TCT GGC TTT
  AGT AAT AGT AGT GTA AGT ATA ATA AGA GCT

The net result of this change is that the aspartic residue at position 411 in the toxin encoded by pEW3 (Table 1A, SEQ ID NO:2) is converted to asparagine, and the glycine residue at position 425 is converted to a glutamic residue. All other amino acids encoded by these genes are identical.

The changes made at positions 411 and 425, discussed above, clearly illustrate the sensitivity of these two positions in toxin EW3. Accordingly, the scope of the invention is not limited to the particular amino acids depicted as participating in the changes. The scope of the invention includes substitution of all 19 other amino acids at these positions. This can be shown by the following schematic:

```
    NH2                 NH2
     |                   |
     |                   |
    411-Asp  ———▶  411-X
     |                   |
    425-Gly  ———▶  425-Y
     |                   |
     |                   |
    COOH               COOH
    EW3
``` wherein X is one of the 20 common amino acids except Asp when the amino acid at position 425 is Gly; Y is one of the 20 common amino acids except Gly when the amino acids at position 411 is Asp. The 20 common amino acids are as follows: alanine, arginine, asparagine, aspartate, cysteine, glutamine, glutamate, glycine, histidine, isoleucine, leucine, lysine, methionine, phenylalanine, proline, serine, threonine, tryptophan, tyrosine, and valine.

EXAMPLE 8

Chimeric Toxin Denoted SYW1

Enhanced toxicity against tested insects was shown by a toxin denoted SYW1. The toxin SYW1 (Table 4A, SEQ ID NO:8) is encoded by plasmid pSYW1 (Table 4, SEQ ID NO:7). The insecticidal activity encoded by pSYW1, in comparison with pEW1 (Example 1) and pEW2 (Example 2), is as follows:

| | $LC_{50}$ (O.D.$_{575}$/ml) | | |
|---|---|---|---|
| Clone | T. ni | H. zea | S. exigua |
| pEW1 | 3.5 | 12.3 | 18.8 |
| pEW2 | 1.4 | 52.3 | 5.9 |
| pSYW1 | 0.7 | 1.9 | 12.0 |

The above test was conducted using the conditions described previously.

Plasmid pSYW1 was constructed as follows:

Plasmid DNA from pEW2 was prepared by standard procedures and submitted to complete digestion with restriction enzyme AsuII followed by partial digestion with EcoRI. A 5878 bp fragment was purified by electroelution following agarose gel electrophoresis of the digest by standard procedures.

Plasmid DNA from strain HD-1 was prepared and submitted to complete digestion with restriction enzymes AsuII and EcoRI. A 222 bp fragment was purified by electroelution following agarose gel electrophoresis of the digest.

The two fragments (5878 bp from pEW2 and 222 bp from HD-1) were ligated together, by standard procedures, to form construct pSYW1.

The amino acid changes (3) in toxin SYW1 from EW3 are as follows: (1) Arginine residue 289 in EW3 was changed to glycine in SWY1, (2) arginine residue 311 in EW3 was changed to lysine in SYW1, and (3) the tyrosine residue 313 was changed to glycine in SYW1. A schematic representation of these two toxins is as follows:

```
NH₂                NH₂
 |                  |
 |                  |
 |                  |
289-Arg  ────▶  289-Gly
 |                  |
311-Arg  ────▶  311-Lys
 |                  |
313-Tyr  ────▶  313-Glu
 |                  |
 |                  |
 |                  |
COOH               COOH
EW3                SYW1
```

The changes made at positions 289, 311, and 313, discussed above, clearly illustrate the sensitivity of these three positions in toxin EW3. Accordingly, the scope of the invention is not limited to the particular amino acids depicted as participating in the changes. The scope of the invention includes substitution of all the common amino acids at these positions. This can be shown by the following schematic:

```
NH₂                NH₂
 |                  |
 |                  |
 |                  |
289-Arg  ────▶  289-X
 |                  |
311-Arg  ────▶  311-Y
 |                  |
313-Tyr  ────▶  313-Z
 |                  |
 |                  |
 |                  |
COOH               COOH
EW3
``` wherein X is one of the 20 common amino acids except Arg when the amino acid at position 311 is Arg and the amino acid at position 313 is Tyr; Y is one of the 20 common amino acids except Arg when the amino acid at position 289 is Arg and the amino acid at position 313 is Tyr; and Z is one of the 20 common amino acids except Tyr when the amino acid at position 289 is Arg and the amino acid at position 311 is Arg.

Construction of the SYW1 gene can be carried out by procedures disclosed above for the construction of the ACB-1 gene from plasmid pEW3 with appropriate changes in the synthetic DNA oligomer.

As is well known in the art, the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| Phenylalanine (Phe) | TTK | Histidine (His) | CAK |
|---|---|---|---|
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence corresponds to the mRNA sequence, with thymine substituted for uracil. The letters stand for the purine or pyrimidine bases forming the deoxynucleotide sequence.

A=Adenine
G=guanine
C=cytosine
T=thymine
X=T or C if Y is A or G
S=C if Y is C or T
Y=A, G, C or T if X is C
Y=A or G if X is T
W=C or A if Z is A or G
W=C if Z is C or T
Z=A, G, C or T if W is C
Z=A or G if W is A
QR=TC if S is A, G, C or T; alternatively QR=AG if S is T or C
J=A or G
K=T or C
L=A, T, C or G
M=A, C or T The above shows that the novel amino acid sequence of the chimeric toxins, and other useful proteins, can be prepared by equivalent nucleotide sequences encoding the same amino acid sequence of the proteins. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes muteins of the amino acid sequences depicted herein which do not alter the protein secondary structure.

The one-letter symbol for the amino acids used in Tables 1A and 2A is well known in the art. For convenience, the relationship of the three-letter abbreviation and the one-letter symbol for amino acids is as follows:

| Ala | A |
|---|---|
| Arg | R |
| Asn | N |

| | |
|---|---|
| Asp | D |
| Cys | C |
| Gln | Q |
| Glu | E |
| Gly | G |
| His | H |
| Ile | I |
| Leu | L |
| Lys | K |
| Met | M |
| Phe | F |
| Pro | P |
| Ser | S |
| Thr | T |
| Trp | W |
| Tyr | Y |
| Val | V |

The work described herein was all done in conformity with physical and biological containment requirements specified in the NIH Guidelines.

CHART A
Bioassay of Chimeric Toxins Against Various Insects

| | | LC50 (O.D. 575/ml diet) | | |
|---|---|---|---|---|
| Plasmid | Toxin | T. ni | S. exigua | H. zea |
| pEW1 | k-1 | 3.5 | 12.3 | 18.8 |
| pEW2 | k-73 | 1.4 | 52.3 | 5.9 |
| pEW3 | k-73/k-1 | 5.7 | 9.6 | 10.4 |
| pEW4 | k-1/k-73 | 0.8 | 30.4 | 2.2 |

Recombinant E. coli cells containing the above plasmids were grown overnight in L-broth.* The cells were pelleted and resuspended on 0.85% NaCl. The optical density at 575 nm was determined for these cell suspensions and appropriate dilutions were made in 0.85% NaCl. Three ml of each dilution were added to 27 ml of USDA diet (Dulmage, H. D., Martinez, A. J. and Pena, T [1976] USDA Agricultural Research Service Technical Bulletin No. 1528, U.S. Government Printing Office, Washington, D.C.). The diet/toxin mixture was then dispensed into 24 wells in a plastic tissue culture tray (1.0 ml/well). Single neonate larvae from either Trichoplusia ni, Spodoptera exigua, or Heliothis zea were then added to each well. The trays were then covered with Mylar and punctured with small holes for air exchange. The larvae were observed after 7 days and LC50 values were calculated using the method of probit analysis (Finney, D. J. [1971] Probit Analysis 3rd ed. Cambridge University Press, Cambridge).
*L-broth is 5 g/l NaCl, 10 g/l bactotryptone, 5 g/l yeast extract.

CHART B
Assay of Toxins Against CF-1 Cells in Culture

| | | Live Cells (% of Control) | |
|---|---|---|---|
| Plasmid | Toxin | Expt. 1 | Expt. 2 |
| pEW1 | k-1 | 106% | 108% |
| pEW2 | k-73 | 44% | 46% |
| pEW3 | k-73/k-1 | 105% | 97% |
| pEW4 | k-1/k-73 | 53% | 58% |

Overnight cultures of E. coli containing the various plasmids were centrifuged and resuspended in 0.85% NaCl containing 1 mM EDTA[1], 0.2 mM PMSF[2], 0.2 mM TPCK[3] and 100 mM NaOH. Cells were broken in a bead beater (Biospec Products, Bartlesville, OK), centrifuged and the supernatant dialyzed against 20 mM Tris-glycine pH 8.5. Toxin was activated with 0.7% trypsin. Assays were carried out on Choristoneura fumiferana cell line CF-1. Approximately 100 μg of activated toxin extract was added to $3.2 \times 10^5$ cells in a volume of 1.0 ml. ATP levels were determined after 30 min incubation and the percentage of live cells remaining in the suspension was determined from standard curves.

[1]ethylenediaminetetraacetic acid
[2]phenylmethylsulfonyl fluoride
[3]1-tosylamide-2-phenylethylchloromethyl ketone CHART C
Facile Comparison of Constructions of Plasmids pEW3 and pEW4

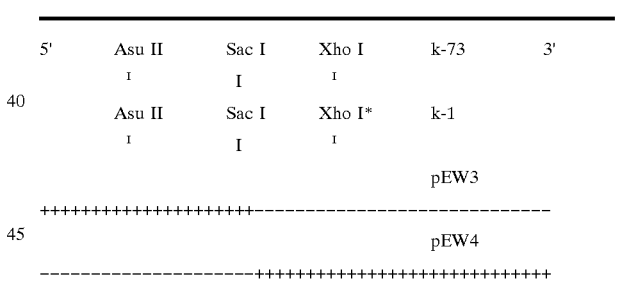

---- = sequences from k-1
++++ = sequences from k-73

Xho I* means that this restriction site found in k-73 no longer exists in k-1 and will have to be recreated by site specific mutagenesis (it involves changing two base pairs in k-1).

TABLE 1

| Nucleotide Sequence of Plasmid pEW3 Encoding Chimeric Toxin (SEQ ID NO: 1) | | | | | |
|---|---|---|---|---|---|
| | (start HD-73) | | | ATG | GATAACAATC | 400 |
| CGAACATCAA | TGAATGCATT | CCTTATAATT | GTTTAAGTAA | CCCTGAAGTA | |
| GAAGTATTAG | GTGGAGAAAG | AATAGAAACT | GGTTACACCC | CAATCGATAT | 500 |
| TTCCTTGTCG | CTAACGCAAT | TTCTTTTGAG | TGAATTTGTT | CCCGGTGCTG | |
| GATTTGTGTT | AGGACTAGTT | GATATAAATAT | GGGGAATTTT | TGGTCCCTCT | 600 |
| CAATGGGACG | CATTTCTTGT | ACAAATTGAA | CAGTTAATTA | ACCAAAGAAT | |
| AGAAGAATTC | GCTAGGAACC | AAGCCATTTC | TAGATTAGAA | GGACTAAGCA | 700 |
| ATCTTTATCA | AATTTACGCA | GAATCTTTTA | GAGAGTGGGA | AGCAGATCCT |  |

TABLE 1-continued

Nucleotide Sequence of Plasmid pEW3 Encoding Chimeric Toxin (SEQ ID NO: 1)

| | | | | | |
|---|---|---|---|---|---|
| ACTAATCCAG | CATTAAGAGA | AGAGATGCGT | ATTCAATTCA | ATGACATGAA | 800 |
| CAGTGCCCTT | ACAACCGCTA | TTCCTCTTTT | TGCAGTTCAA | AATTATCAAG | |
| TTCCTCTTTT | ATCAGTATAT | GTTCAAGCTG | CAAATTTACA | TTTATCAGTT | 900 |
| TTGAGAGATG | TTTCAGTGTT | TGGACAAAGG | TGGGGATTTG | ATGCCGCGAC | |
| TATCAATAGT | CGTTATAATG | ATTTAACTAG | GCTTATTGGC | AACTATACAG | 1000 |
| ATTATGCTGT | ACGCTGGTAC | AATACGGGAT | TAGAACGTGT | ATGGGGACCG | |
| GATTCTAGAG | ATTGGGTAAG | GTATAATCAA | TTTAGAAGAG | AATTAACACT | 1100 |
| AACTGTATTA | GATATCGTTG | CTCTGTTCCC | GAATTATGAT | AGTAGAAGAT | |
| ATCCAATTCG | AACAGTTTCC | CAATTAACAA | GAGAAATTTA | TACAAACCCA | 1200 |
| GTATTAGAAA | ATTTTGATGG | TAGTTTTCGA | GGCTCGGCTC | AGGGCATAGA | |
| AAGAAGTATT | AGGAGTCCAC | ATTTGATGGA | TATACTTAAC | AGTATAACCA | 1300 |
| TCTATACGGA | TGCTCATAGG | GGTTATTATT | ATTGGTCAGG | GCATCAAATA | |
| ATGGCTTCTC | CTGTAGGGTT | TTCGGGGCCA | GAATTCACTT | TTCCGCTATA | 1400 |
| TGGAACTATG | GGAAATGCAG | CTCCACAACA | ACGTATTGTT | GCTCAACTAG | |
| GTCAGGGCGT | GTATAGAACA | TTATCGTCCA | CTTTATATAG | AAGACCTTTT | 1500 |
| AATATAGGGA | TAAATAATCA | ACAACTATCT | GTTCTTGACG | GGACAGAATT | |
| TGCTTATGGA | ACCTCCTCAA | ATTTGCCATC | CGCTGTATAC | AGAAAAAGCG | 1600 |
| GAACGGTAGA | TTCGCTGGAT | GAAATACCGC | CACAGAATAA | CAACGTGCCA | |
| CCTAGGCAAG | GATTTAGTCA | TCGATTAAGC | CATGTTTCAA | TGTTTCGTTC | 1700 |
| AGGCTTTAGT | AATAGTAGTG | TAAGTATAAT | AAGAGCT (end hd-73) | | |
| (start HD-1) | | CCAACGT | TTTCTTGGCA | GCATCGCAGT | 1900 |
| GCTGAATTTA | ATAATATAAT | TCCTTCATCA | CAAATTACAC | AAATACCTTT | |
| AACAAAATCT | ACTAATCTTG | GCTCTGGAAC | TTCTGTCGTT | AAAGGACCAG | 2000 |
| GATTTACAGG | AGGAGATATT | CTTCGAAGAA | CTTCACCTGG | CCAGATTTCA | |
| ACCTTAAGAG | TAAATATTAC | TGCACCATTA | TCACAAAGAT | ATCGGGTAAG | 2100 |
| AATTCGCTAC | GCTTCTACTA | CAAATTTACA | ATTCCATACA | TCAATTGACG | |
| GAAGACCTAT | TAATCAGGGT | AATTTTTCAG | CAACTATGAG | TAGTGGGAGT | 2200 |
| AATTTACAGT | CCGGAAGCTT | TAGGACTGTA | GGTTTTACTA | CTCCGTTTAA | |
| CTTTTCAAAT | GGATCAAGTG | TATTTACGTT | AAGTGCTCAT | GTCTTCAATT | 2300 |
| CAGGCAATGA | AGTTTATATA | CATCGAATTG | AATTTGTTCC | GGCAGAAGTA | |
| ACCTTTGAGG | CAGAATATGA | TTTAGAAAGA | GCACAAAAGG | CGGTGAATGA | 2400 |
| GCTGTTTACT | TCTTCCAATC | AAATCGGGTT | AAAAACAGAT | GTGACGGATT | |
| ATCATATTGA | TCAAGTATCC | AATTTAGTTG | AGTGTTTATC | AGATGAATTT | 2500 |
| TGTCTGGATG | AAAAACAAGA | ATTGTCCGAG | AAAGTCAAAC | ATGCGAAGCG | |
| ACTTAGTGAT | GAGCGGAATT | TACTTCAAGA | TCCAAACTTC | AGAGGGATCA | 2600 |
| ATAGACAACT | AGACCGTGGC | TGGAGAGGAA | GTACGGATAT | TACCATCCAA | |
| GGAGGCGATG | ACGTATTCAA | AGAGAATTAC | GTTACGCTAT | TGGGTACCTT | 2700 |
| TGATGGTGC | TATCCAACGT | ATTTATATCA | AAAAATAGAT | GAGTCGAAAT | |
| TAAAAGCCTA | TACCCGTTAT | CAATTAAGAG | GGTATATCGA | AGATAGTCAA | 2800 |
| GACTTAGAAA | TCTATTTAAT | TCGCTACAAT | GCAAAACATG | AAACAGTAAA | |
| TGTGCCAGGT | ACGGGTTCCT | TATGGCCGCT | TTCAGCCCAA | AGTCCAATCG | 2900 |
| GAAAGTGTGG | AGAGCCGAAT | CGATGCGCGC | CACACCTTGA | ATGGAATCCT | |
| GACTTAGATT | GTTCGTGTAG | GGATGGAGAA | AAGTGTGCCC | ATCATTCGCA | 3000 |
| TCATTTCTCC | TTAGACATTG | ATGTAGGATG | TACAGACTTA | AATGAGGACC | |
| TAGGTGTATG | GGTGATCTTT | AAGATTAAGA | CGCAAGATGG | GCACGCAAGA | 3100 |
| CTAGGGAATC | TAGAGTTTCT | CGAAGAGAAA | CCATTAGTAG | GAGAAGCGCT | |
| AGCTCGTGTG | AAAAGAGCGG | AGAAAAAATG | GAGAGACAAA | CGTGAAAAAT | 3200 |
| TGGAATGGGA | AACAAATATC | GTTTATAAAG | AGGCAAAAGA | ATCTGTAGAT | |
| GCTTTATTTG | TAAACTCTCA | ATATGATCAA | TTACAAGCGG | ATACGAATAT | 3300 |
| TGCCATGATT | CATGCGGCAG | ATAAACGTGT | TCATAGCATT | CGAGAAGCTT | |
| ATCTGCCTGA | GCTGTCTGTT | ATTCCGGGTG | TCAATGCGGC | TATTTTTGAA | 3400 |
| GAATTAGAAG | GGCGTATTTT | CACTGCATTC | TCCCTATATG | ATGCGAGAAA | |
| TGTCATTAAA | AATGGTGATT | TTAATAATGG | CTTATCCTGC | TGGAACGTGA | 3500 |
| AAGGGCATGT | AGATGTAGAA | GAACAAAACA | ACCAACGTTC | GGTCCTTGTT | |
| CTTCCGGAAT | GGGAAGCAGA | AGTGTCACAA | GAAGTTCGTG | TCTGTCCGGA | 3600 |
| TCGTGGCTAT | ATCCTTCGTG | TCACAGCGTA | CAAGGAGGGA | TATGGAGAAG | |
| GTTGCGTAAC | CATTCATGAG | ATCGAGAACA | ATACAGACGA | ACTGAAGTTT | 3700 |
| AGCAACTGCG | TAGAAGAGGA | AATCTATCCA | AATAACACGG | TAACGTGTAA | |
| TGATTATACT | GTAAATCAAG | AAGAATACGG | AGGTGCGTAC | ACTTCTCGTA | 3800 |
| ATCGAGGATA | TAACGAAGCT | CCTTCCGTAC | CAGCTGATTA | TGCGTCAGTC | |
| TATGAAGAAA | AATCGTATAC | AGATGGACGA | AGAGAGAATC | CTTGTGAATT | 3900 |
| TAACAGAGGG | TATAGGGATT | ACACGCCACT | ACCAGTTGGT | TATGTGACAA | |
| AAGAATTAGA | ATACTTCCCA | GAAACCGATA | AGGTATGGAT | TGAGATTGGA | 4000 |
| GAAACGGAAG | GAACATTTAT | CGTGGACAGC | GTGGAATTAC | TCCTTATGGA | |
| GGAA (end HD-1) | | | | | |

Numbering of the nucleotide bases is the same as Schnepf et al. (J. Biol. Chem. 260:6264–6272 [1985]) for HD-1 and Adang et al. (Gene 36:289–300 [1985]) for HD-73. Only protein coding sequences are shown.

TABLE 1A

Deduced Amino Acid Sequence of Chimeric Toxin Produced by Plasmid pEW3 (SEQ ID NO: 2)

M D N N P N I N E C I P Y N C L S N P E V E V L G G E R I E
T G Y T P I D I S L S L T Q F L L S E F V P G A G F V L G L
V D I I W G I F G P S Q W D A F L V Q I E Q L I N Q R I E E
F A R N Q A I S R L E G L S N L Y Q I Y A E S F R E W E A D
P T N P A L R E E M R I Q F N D M N S A L T T A I P L F A V
Q N Y Q V P L L S V Y V Q A A N L H L S V L R D V S V F G Q
R W G F D A A T I N S R Y N D L T R L I G N Y T D Y A V R W
Y N T G L E R V W G P D S R D W V R Y N Q F R R E L T L T V
L D I V A L F P N Y D S R R Y P I R T V S Q L T R E I Y T N
P V L E N F D G S F R G S A Q G I E R S I R S P H L M D I L
N S I T I Y T D A H R G Y Y Y W S G H Q I M A S P V G F S G
P E F T F P L Y G T M G N A A P Q Q R I V A Q L G Q G V Y R
T L S S T L Y R R P F N I G I N N Q Q L S V L D G T E F A Y
G T S S N L P S A V Y R K S G T V D S L D E I P P Q N N N V
P P R Q G F S H R L S H V S M F R S G F S N S S V S I I R A
P T F S W Q H R S A E F N N I I P S S Q I T Q I P L T K S T
N L G S G T S V V K G P G F T G G D I L R R T S P G Q I S T
L R V N I T A P L S Q R Y R V R I R Y A S T T N L Q F H T S
I D G R P I N Q G N F S A T M S S G S N L Q S G S F R T V G
F T T P F N F S N G S S V F T L S A H V F N S G N E V Y I D

TABLE 1A-continued

Deduced Amino Acid Sequence of Chimeric Toxin Produced by Plasmid pEW3 (SEQ ID NO: 2)

TABLE 2-continued

Nucleotide Sequence of Plasmid pEW4 Encoding Chimeric Toxin (SEQ ID NO: 3)

| | | | | | |
|---|---|---|---|---|---|
| TACCAGCTAC | AGCTACGTCA | TTAGATAATC | TACAATCAAG | TGATTTTGGT | 2100 |
| TATTTTGAAA | GTGCCAATGC | TTTTACATCT | TCATTAGGTA | ATATAGTAGG | |
| TGTTAGAAAT | TTTAGTGGGA | CTGCAGGAGT | GATAATAGAC | AGATTTGAAT | 2200 |
| TTATTCCAGT | TACTGCAACA | CTCGAGGCTG | AATATAATCT | GGAAAGAGCG | |
| CAGAAGGCGG | TGAATGCGCT | GTTTACGTCT | ACAAACCAAC | TAGGGCTAAA | 2300 |
| AACAAATGTA | ACGGATTATC | ATATTGATCA | AGTGTCCAAT | TTAGTTACGT | |
| ATTTATCGGA | TGAATTTTGT | CTGGATGAAA | AGCGAGAATT | GTCCGAGAAA | 2400 |
| GTCAAACATG | CGAAGCGACT | CAGTGATGAA | CGCAATTTAC | TCCAAGATTC | |
| AAATTTCAAA | GACATTAATA | GGCAACCAGA | ACGTGGGTGG | GGCGGAAGTA | 2500 |
| CAGGGATTAC | CATCCAAGGA | GGGGATGACG | TATTTAAAGA | AAATTACGTC | |
| ACACTATCAG | GTACCTTTGA | TGAGTGCTAT | CCAACATATT | TGTATCAAAA | 2600 |
| AATCGATGAA | TCAAAATTAA | AAGCCTTTAC | CCGTTATCAA | TTAAGAGGGT | |
| ATATCGAAGA | TAGTCAAGAC | TTAGAAATCT | ATTTAATTCG | CTACAATGCA | 2700 |
| AAACATGAAA | CAGTAAATGT | GCCAGGTACG | GGTTCCTTAT | GGCCGCTTTC | |
| AGCCCAAAGT | CCAATCGGAA | AGTGTGGAGA | GCCGAATCGA | TGCGCGCCAC | 2800 |
| ACCTTGAATG | GAATCCTGAC | TTAGATTGTT | CGTGTAGGGA | TGGAGAAAAG | |
| TGTGCCCATC | ATTCGCATCA | TTTCTCCTTA | GACATTGATG | TAGGATGTAC | 2900 |
| AGACTTAAAT | GAGGACCTAG | GTGTATGGGT | GATCTTTAAG | ATTAAGACGC | |
| AAGATGGGCA | CGCAAGACTA | GGGAATCTAG | AGTTTCTCGA | AGAGAAACCA | 3000 |
| TTAGTAGGAG | AAGCGCTAGC | TCGTGTGAAA | AGAGCGGAGA | AAAAATGGAG | |
| AGACAAACGT | GAAAAATTGG | AATGGGAAAC | AAATATCGTT | TATAAAGAGG | 3100 |
| CAAAAGAATC | TGTAGATGCT | TTATTTGTAA | ACTCTCAATA | TGATCAATTA | |
| CAAGCGGATA | CGAATATTGC | CATGATTCAT | GCGGCAGATA | AACGTGTTCA | 3200 |
| TAGCATTCGA | GAAGCTTATC | TGCCTGAGCT | GTCTGTGATT | CCGGGTGTCA | |
| ATGCGGCTAT | TTTTGAAGAA | TTAGAAGGGC | GTATTTTCAC | TGCATTCTCC | 3300 |
| CTATATGATG | CGAGAAATGT | CATTAAAAAT | GGTGATTTTA | ATAATGGCTT | |
| ATCCTGCTGG | AACGTGAAAG | GGCATGTAGA | TGTAGAAGAA | CAAAACAACC | 3400 |
| AACGTTCGGT | CCTTGTTGTT | CCGGAATGGG | AAGCAGAAGT | GTCACAAGAA | |
| GTTCGTGTCT | GTCCGGGTCG | TGGCTATATC | CTTCGTGTCA | CAGCGTACAA | 3500 |
| GGAGGGATAT | GGAGAAGGTT | GCGTAACCAT | TCATGAGATC | GAGAACAATA | |
| CAGACGAACT | GAAGTTTAGC | AACTGCGTAG | AAGAGGAAAT | CTATCCAAAT | 3600 |
| AACACGGTAA | CGTGTAATGA | TTATACTGTA | AATCAAGAAG | AATACGGAGG | |
| TGCGTACACT | TCTCGTAATC | GAGGATATAA | CGAAGCTCCT | TCCGTACCAG | 3700 |
| CTGATTATGC | GTCAGTCTAT | GAAGAAAAAT | CGTATACAGA | TGGACGAAGA | |
| GAGAATCCTT | GTGAATTTAA | CAGAGGGTAT | AGGGATTACA | CGCCACTACC | 3800 |
| AGTTGGTTAT | GTGACAAAAG | AATTAGAATA | CTTCCCAGAA | ACCGATAAGG | |
| TATGGATTGA | GATTGGAGAA | ACGGAAGGAA | CATTTATCGT | GGACAGCGTG | 3900 |
| GAATTACTCC | TTATGGAGGA | A (end HD-73) | | | |

Numbering of nucleotide bases is the same as Schnepf et al. (J. Biol. Chem. 260:6264–6272 [1985]) for HD-1 and Adang et al. (Gene 36:289–300 [1985]) for HD-73. Only protein coding sequences are shown.

TABLE 2A

Deduced Amino Acid Sequence of Chimeric Toxin Produced by Plasmid pEW4 (SEQ ID NO: 4)

MDNNPNINECIPYNCLSNPEVEVLGGERIE
TGYTPIDISLSLTQFLLSEFVPGAGFVLGL
VDIIWGIFGPSQWDAFPVQIEQLINQRIEE
FARNQAISRLEGLSNLYQIYAESFREWEAD
PTNPALREEMRIQFNDMNSALTTAIPLLAV
QNYQVPLLSVYVQAANLHLSVLRDVSVFGQ
RWGFDAATINSRYNDLTRLIGNYTDYAVRW
YNTGLERVWGPDSRDWVRYNQFRRELTLTV
LDIVALFSNYDSRRYPIRTVSQLTREIYTN
PVLENFDGSFRGMAQRIEQNIRQPHLMDIL
NSITIYTDVHRGFNYWSGHQITASPVGFSG
PEFAFPLFGNAGNAAPPVLVSLTGLGIFRT
LSSPLYRRIILGSGPNNQELFVLDGTEFSF
ASLTTNLPSTIYRQRGTVDSLDVIPPQDNS
VPPRAGFSHRLSHVTMLSQAAGAVYTLRAQ
RPMFSWIHRSAEFNNIIASDSITQIPAVKG
NFLFNGSVISGPGFTGGDLVRLNSSGNNIQ
NRGYIEVPIHFPSTSTRYRVRVRYASVTPI
HLNVNWGNSSIFSNTVPATATSLDNLQSSD
FGYFESANAFTSSLGNIVGVRNFSGTAGVI
IDRFRFIPVTATLEAEYNLERAQKAVNALF
TSTNQLGLKTNVTDYHIDQVSNLVTYLSDE
FCLDEKRELSEKVKHAKRLSDERNLLQDSN
FKDINRQPERGWGGSTGITIQGGDDVFKEN
YVTLSGTFDECYPTYLYQKIDESKLKAFTR
YQLRGYIEDSQDLEIYLIRYNAKHETVNVP
GTGSLWPLSAQSPIGKCGEPNRCAPHLEWN
PDLDCSCRDGEKCAHHSHHFSLDIDVGCTD
LNEDLGVWVIFKIKTQDGHARLGNLEFLEE
KPLVGEALARVKRAEKKWRDKREKLEWETN
IVYKEAKESVDALFVNSQYDQLQADTNIAM
IHAADKRVHSIREAYLPELSVIPGVNAAIF
EELEGRIFTAFSLYDARNVIKNGDFNNGLS
CWNVKGHVDVEEQNNQRSVLVVPEWEAEVS
QEVRVCPGRGYILRVTAYKEGYGEGCVTIH
EIENNTDELKFSNCVEEEIYPNNTVTCNDY
TVNQEEYGGAYTSRNRGYNEAPSVPADYAS
VYEEKSYTDGRRENPCEFNRGYRDYTPLPV
GYVTKELEYFPETDKVWIEIGETEGTFIVD
SVELLLMEE

TABLE 3

Nucleotide Sequence of Plasmid pACB-1 Encoding Chimeric Toxin ACB-1 (SEQ ID NO: 5)

| | | | | | |
|---|---|---|---|---|---|
| | | HD-73) | ATG | GATAACAATC | 400 |
| CGAACATCAA | TGAATGCATT | CCTTATAATT | GTTTAAGTAA | CCCTGAAGTA | |
| GAAGTATTAG | GTGGAGAAAG | AATAGAAACT | GGTTACACCC | CAATCGATAT | 500 |
| TTCCTTGTCG | CTAACGCAAT | TTCTTTTGAG | TGAATTTGTT | CCCGGTGCG | |
| GATTTGTGTT | AGGACTAGTT | GATATAATAT | GGGGAATTTT | TGGTCCCTCT | 600 |
| CAATGGGACG | CATTTCTTGT | ACAAATTGAA | CAGTTAATTA | ACCAAAGAAT | |
| AGAAGAATTC | GCTAGGAACC | AAGCCATTTC | TAGATTAGAA | GGACTAAGCA | 700 |
| ATCTTTATCA | AATTTACGCA | GAATCTTTTA | GAGAGTGGGA | AGCAGATCCT | |
| ACTAATCCAG | CATTAAGAGA | AGAGATGCGT | ATTCAATTCA | ATGACATGAA | 800 |
| CAGTGCCCTT | ACAACCGCTA | TTCCTCTTTT | TGCAGTTCAA | AATTATCAAG | |
| TTCCTCTTTT | ATCAGTATAT | GTTCAAGCTG | CAAATTTACA | TTTATCAGTT | 900 |
| TTGAGAGATG | TTTCAGTGTT | TGGACAAAGG | TGGGGATTTG | ATGCCGCGAC | |
| TATCAATAGT | CGTTATAATG | ATTTAACTAG | GCTTATTGGC | AACTATACAG | 1000 |
| ATTATGCTGT | ACGCTGGTAC | AATACGGGAT | TAGAACGTGT | ATGGGGACCG | |
| GATTCTAGAG | ATTGGGTAAG | GTATAATCAA | TTTAGAAGAG | AATTAACACT | 1100 |
| AACTGTATTA | GATATCGTTG | CTCTGTTCCC | GAATTATGAT | AGTAGAAGAT | |
| ATCCAATTCG | AACAGTTTCC | CAATTAACAA | GAGAAATTTA | TACAAACCCA | 1200 |
| GTATTAGAAA | ATTTTGATGG | TAGTTTTCGA | GGCTCGGCTC | AGGGCATAGA | |
| AAGAAGTATT | AGGAGTCCAC | ATTTGATGGA | TATACTTAAC | AGTATAACCA | 1300 |
| TCTATACGGA | TGCTCATAGG | GGTTATTATT | ATTGGTCAGG | GCATCAAATA | |
| ATGGCTTCTC | CTGTAGGGTT | TTCGGGGCCA | GAATTCACTT | TTCCGCTATA | 1400 |
| TGGAACTATG | GGAAATGCAG | CTCCACAACA | ACGTATTGTT | GCTCAACTAG | |
| GTCAGGGCGT | GTATAGAACA | TTATCGTCCA | CTTTATATAG | AAGACCTTTT | 1500 |
| AATATAGGGA | TAAATAATCA | ACAACTATCT | GTTCTTGACG | GGACAGAATT | |
| TGCTTATGGA | ACCTCCTCAA | ATTTGCCATC | CGCTGTATAC | AGAAAAAGCG | 1600 |
| GAACGGTAGA | TTCGCTGAAT | GAAATACCGC | CACAGAATAA | CAACGTGCCA | |
| CCTAGGCAAG | AATTTAGTCA | TCGATTAAGC | CATGTTTCAA | TGTTTCGTTC | 1700 |
| AGGCTTTAGT | AATAGTAGTG | TAAGTATAAT | AAGAGCT (end hd-73) | | |
| | (start HD-1) | CCAACGT | TTTCTTGGCA | GCATCGCAGT | 1900 |
| GCTGAATTTA | ATAATATAAT | TCCTTCATCA | CAAATTACAC | AAATACCTTT | |
| AACAAAATCT | ACTAATCTTG | GCTCTGGAAC | TTCTGTCGTT | AAAGGACCAG | 2000 |
| GATTTACAGG | AGGAGATATT | CTTCGAAGAA | CTTCACCTGG | CCAGATTTCA | |
| ACCTTAAGAG | TAAATATTAC | TGCACCATTA | TCACAAAGAT | ATCGGGTAAG | 2100 |
| AATTCGCTAC | GCTTCTACTA | CAAATTTACA | ATTCCATACA | TCAATTGACG | |
| GAAGACCTAT | TAATCAGGGT | AATTTTTCAG | CAACTATGAG | TAGTGGGAGT | 2200 |
| AATTTACAGT | CCGGAAGCTT | TAGGACTGTA | GGTTTTACTA | CTCCGTTTAA | |
| CTTTTCAAAT | GGATCAAGTG | TATTTACGTT | AAGTGCTCAT | GTCTTCAATT | 2300 |
| CAGGCAATGA | AGTTTATATA | GATCGAATTG | AATTTGTTCC | GGCAGAAGTA | |
| ACCTTTGAGG | CAGAATATGA | TTTAGAAAGA | GCACAAAAGG | CGGTGAATGA | 2400 |
| GCTGTTTACT | TCTTCCAATC | AAATCGGGTT | AAAAACAGAT | GTGACGGATT | |
| ATCATATTGA | TCAAGTATCC | AATTTAGTTG | AGTGTTTATC | AGATGAATTT | 2500 |
| TGTCTGGATG | AAAAACAAGA | ATTGTCCGAG | AAAGTCAAAC | ATGCGAAGCG | |
| ACTTAGTGAT | GAGCGGAATT | TACTTCAAGA | TCCAAACTTC | AGAGGGATCA | 2600 |
| ATAGACAACT | AGACCGTGGC | TGGAGAGGAA | GTACGGATAT | TACCATCCAA | |
| GGAGGCGATG | ACGTATTCAA | AGAGAATTAC | GTTACGCTAT | TGGGTACCTT | 2700 |
| TGATGAGTGC | TATCCAACGT | ATTTATATCA | AAAAATAGAT | GAGTCGAAAT | |
| TAAAAGCCTA | TACCCGTTAT | CAATTAAGAG | GGTATATCGA | AGATAGTCAA | 2800 |
| GACTTAGAAA | TCTATTTAAT | TCGCTACAAT | GCAAAACATG | AAACAGTAAA | |
| TGTGCCAGGT | ACGGGTTCCT | TATGGCCGCT | TTCAGCCCAA | AGTCCAATCG | 2900 |
| GAAAGTGTGG | AGAGCCGAAT | CGATGCGCGC | CACACCTTGA | ATGGAATCCT | |
| GACTTAGATT | GTTCGTGTAG | GGATGGAGAA | AAGTGTGCCC | ATCATTCGCA | 3000 |
| TCATTTCTCC | TTAGACATTG | ATGTAGGATG | TACAGACTTA | AATGAGGACC | |
| TAGGTGTATG | GGTGATCTTT | AAGATTAAGA | CGCAAGATGG | GCACGCAAGA | 3100 |
| CTAGGGAATC | TAGAGTTTCT | CGAAGAGAAA | CCATTAGTAG | GAGAAGCGCT | |
| AGCTCGTGTG | AAAAGAGCGG | AGAAAAAATG | GAGAGACAAA | CGTGAAAAAT | 3200 |
| TGGAATGGGA | AACAAATATC | GTTTATAAAG | AGGCAAAAGA | ATCTGTAGAT | |
| GCTTTATTTG | TAAACTCTCA | ATATGATCAA | TTACAAGCGG | ATACGAATAT | 3300 |
| TGCCATGATT | CATGCGGCAG | ATAAACGTGT | TCATAGCATT | CGAGAAGCTT | |
| ATCTGCCTGA | GCTGTCTGTG | ATTCCGGGTG | TCAATGCGGC | TATTTTTGAA | 3400 |
| GAATTAGAAG | GGCGTATTTT | CACTGCATTC | TCCCTATATG | ATGCGAGAAA | |
| TGTCATTAAA | AATGGTGATT | TTAATAATGG | CTTATCCTGC | TGGAACGTGA | 3500 |
| AAGGGCATGT | AGATGTAGAA | GAACAAAACA | ACCAACGTTC | GGTCCTTGTT | |
| CTTCCGGAAT | GGGAAGCAGA | AGTGTCACAA | GAAGTTCGTG | TCTGTCCGGG | 3600 |
| TCGTGGCTAT | ATCCTTCGTG | TCACAGCGTA | CAAGGAGGGA | TATGGAGAAG | |
| GTTGCGTAAC | CATTCATGAG | ATCGAGAACA | ATACAGACGA | ACTGAAGTTT | 3700 |
| AGCAACTGCG | TAGAAGAGGA | AATCTATCCA | AATAACACGG | TAACGTGTAA | |
| TGATTATACT | GTAAATCAAG | AAGAATACGG | AGGTGCGTAC | ACTTCTCGTA | 3800 |
| ATCGAGGATA | TAACGAAGCT | CCTTCCGTAC | CAGCTGATTA | TGCGTCAGTC | |
| TATGAAGAAA | AATCGTATAC | AGATGGACGA | AGAGAGAATC | CTTGTGAATT | 3900 |
| TAACAGAGGG | TATAGGGATT | ACACGCCACT | ACCAGTTGGT | TATGTCACAA | |
| AAGAATTAGA | ATACTTCCCA | GAAACCGATA | AGGTATGGAT | TGAGATTGGA | 4000 |
| GAAACGGAAG | GAACATTTAT | CGTGGACAGC | GTGGAATTAC | TCCTTATGGA | |
| GGAA (end HD-1) | | | | | |

The nucleotide differences as compared to the sequence shown in Table 1 are underlined at positions 1618 and 1661 and code for amino acid changes at positions 411 and 425 as shown in TABLE 3A.

TABLE 3A

Deduced Amino Acid Sequence of Chimeric Toxin ACB-1 (SEQ ID NO: 6)

MDNNPNINECIPY

TABLE 4-continued

Nucleotide Sequence of Plasmid pSYW1 Encoding Chimeric Toxin SYW1 (SEQ ID NO: 7)

| | | | | | |
|---|---|---|---|---|---|
| AATTTACAGT | CCGGAAGCTT | TAGGAC

We claim:

1. A process for identifying a recombinant DNA sequence encoding a modified B.t. crystal protein toxin which has an altered host range or increased toxicity against at least one target lepidopteran insect host comprising the steps of:
   (a) replacing at least a part of a variable region of a first parent DNA sequence encoding a lepidopteran active B.t. crystal protein toxin with at least a part of a variable region of at least one other patent DNA sequence encoding a different lepidopteran active B.t. crystal protein toxin to obtain a recombinant DNA sequence encoding a modified B.t. crystal protein toxin which is different from any of said crystal protein toxins encoded by said parent DNA sequences;
   (b) producing said modified B.t. crystal protein toxin from said recombinant DNA sequence; and
   (c) assaying said modified B.t. crystal protein toxin to verify whether said modified B.t. crystal protein toxin has an altered host range or increased toxicity against at least one target lepidopteran insect host as compared to any of said crystal protein toxins encoded by said parent DNA sequences; whereby, if verified, said recombinant DNA sequence is identified as one encoding a modified B.t. crystal protein toxin having an altered host range or increased toxicity.

2. A recombinant DNA sequence encoding a modified B.t. crystal protein toxin which has an altered host range or increased toxicity against at least one target lepidopteran insect host, wherein said recombinant DNA sequence is produced by the process of:
   (a) replacing at least a part of a variable region of a first parent DNA sequence encoding a lepidopteran active B.t. crystal protein toxin with at least a part of a variable region of at least one other parent DNA sequence encoding a different lepidopteran active B.t. crystal protein toxin to obtain a recombinant DNA sequence encoding a modified B.t. crystal protein toxin which is different from any of said crystal protein toxins encoded by said parent DNA sequences;
   (b) producing said modified B.t. crystal protein toxin from said recombinant DNA sequence;
   (c) assaying said modified B.t. crystal protein toxin to verify whether said modified B.t. crystal protein toxin has an altered host range or increased toxicity against at least one target lepidopteran insect host as compared to any of said crystal protein toxins encoded by said parent DNA sequences; whereby, if verified, said recombinant DNA sequence is identified as one encoding a modified B.t. crystal protein toxin having an altered host range or increased toxicity; and (d) obtaining additional copies of said recombinant DNA sequence.

3. A process for identifying a recombinant DNA sequence encoding a modified B.t. crystal protein toxin which has an altered host range or increased toxicity against at least one target lepidopteran insect host comprising the steps of:

(a) replacing at least a part of a variable region of a first parent DNA sequence encoding a lepidopteran active B.t. crystal protein toxin with at least a part of a variable region of at least one other parent DNA sequence encoding a different lepidopteran active B.t. crystal protein toxin to obtain a recombinant DNA sequence encoding a modified B.t. crystal protein toxin which is different from any of said crystal protein toxins encoded by said parent DNA sequences;

(b) producing said modified B.t. crystal protein toxin from said recombinant DNA sequence;

(c) assaying said modified B.t. crystal protein toxin to verify whether said modified B.t. crystal protein toxin has an altered host range or increased toxicity against at least one target lepidopteran insect host as compared to any of said crystal protein toxins encoded by said parent DNA sequences; and (d) repeating the foregoing steps (a)–(c) until said modified B.t. crystal protein is verified to have an altered host range or increased toxicity against at least one target lepidopteran insect host as compared to any of said crystal protein toxins encoded by said parent DNA sequences, whereby the recombinant DNA sequence encoding said modified B.t. crystal protein toxin is identified as one encoding a modified B.t. crystal protein toxin having an altered host range or increased toxicity.

4. A recombinant DNA sequence encoding a modified B.t. crystal protein toxin which has an altered host range or increased toxicity against at least one target lepidopteran insect host, wherein said recombinant DNA sequence is produced by the process of:

(a) replacing at least a part of a variable region of a first parent DNA sequence encoding a lepidopteran active B.t. crystal protein toxin with at least a part of a variable region of at least one other parent DNA sequence encoding a different lepidopteran active B.t. crystal protein toxin to obtain a recombinant DNA sequence encoding a modified B.t. crystal protein toxin which is different from any of said crystal protein toxins encoded by said parent DNA sequences;

(b) producing said modified B.t. crystal protein toxin from said recombinant DNA sequence;

(c) assaying said modified B.t. crystal protein toxin to verify whether said modified B.t. crystal protein toxin has an altered host range or increased toxicity against at least one target lepidopteran insect host as compared to any of said crystal protein toxins encoded by said parent DNA sequences;

(d) repeating the foregoing steps (a)–(c) until said modified B.t. crystal protein is verified to have an altered host range or increased toxicity against at least one target lepidopteran insect host as compared to any of said crystal protein toxins encoded by said parent DNA sequences, whereby the recombinant DNA sequence encoding said modified B.t. crystal protein toxin is identified as one encoding a modified B.t. crystal protein toxin having an altered host range or increased toxicity; and (e) obtaining additional copies of said recombinant DNA sequence.

5. The process of claim 1, wherein the first parent DNA sequence encodes B.t. var. *kurstaki* HD-73 crystal protein toxin, the other parent DNA sequence encodes B.t. var. *kurstaki* HD-1 crystal protein toxin, and the modified B.t. crystal protein toxin has increased insect toxicity to an insect selected from the group consisting of *Trichnoplusia ni, Spodoptera exigua,* and *Heliothis zea.*

6. A recombinant DNA encoding a modified B.t. crystal protein toxin having pesticidal activity, said toxin comprising the amino acid sequence of SEQ ID NO:2.

7. The recombinant DNA according to claim 6, said DNA comprising the nucleotide sequence of SEQ ID NO:1.

* * * * *

UNITED STATES PATENT AND TRADEMARK OFFICE
CERTIFICATE OF CORRECTION

PATENT NO.   : 6,090,931
DATED        : July 18, 2000
INVENTOR(S)  : Edwards et al.

It is certified that error appears in the above-identified patent and that said Letters Patent is hereby corrected as shown below:

Title page,
Item [54], "PROCESS FOR ALTERING THE HOST RANGE OR INCREASING THE TOXICITY OF *BACILLUS THURINGIENSIS* LEPIDOTERAN TOXINS, AND RECOMBINANT DNA SEQUENCES THEREFOR" should read, -- PROCESS FOR ALTERING THE HOST RANGE OR INCREASING THE TOXICITY OF *BACILLUS THURINGIENSIS* LEPIDOTERAN TOXINS, AND RECOMBINANT DNA SEQUENCES THEREFOR --

Column 3,
Line 54, "kursatki" should read -- kurstaki -- .

Column 5,
Line 37, "game." should read -- genome. -- .
Line 56, "lembda" should read -- lambda -- .

Column 8,
Line 33, "position 54" should read -- position 504 -- .
Line 63, "33456" should read -- 3345 -- .

UNITED STATES PATENT AND TRADEMARK OFFICE
CERTIFICATE OF CORRECTION

PATENT NO. : 6,090,931
DATED : July 18, 2000
INVENTOR(S) : Edwards et al.

It is certified that error appears in the above-identified patent and that said Letters Patent is hereby corrected as shown below:

Column 9,
Line 53, "M.D." should read -- M-D. --
Line 64, "Chimeric" should read -- chimeric -- .

Column 11,
Line 19, (schematic): "411-Gly" should read -- 425-Gly -- .

Column 14,
Line 29, "S= C if Y" should read -- X = C if Y -- .

Signed and Sealed this

Twentieth Day of November, 2001

Attest:

*Nicholas P. Godici*

NICHOLAS P. GODICI
*Attesting Officer*    *Acting Director of the United States Patent and Trademark Office*

UNITED STATES PATENT AND TRADEMARK OFFICE
CERTIFICATE OF CORRECTION

PATENT NO.   : 6,090,931
DATED        : July 18, 2000
INVENTOR(S)  : David L. Edwards et al.

It is certified that error appears in the above-identified patent and that said Letters Patent is hereby corrected as shown below:

Title page, Item [54] and Column 1, line 4,
"LEPIDOTERAN TOXINS, AND" should read -- LEPIDOPTERAN ACTIVE TOXINS, AND --.

Column 65,
Line 53, "other patent DNA" should read -- other parent DNA -- .

Signed and Sealed this

Twentieth Day of May, 2003

JAMES E. ROGAN
*Director of the United States Patent and Trademark Office*